(12) United States Patent
Sales et al.

(10) Patent No.: US 10,617,342 B2
(45) Date of Patent: *Apr. 14, 2020

(54) SYSTEMS, APPARATUS, AND METHODS FOR USING A WEARABLE DEVICE TO MONITOR OPERATOR ALERTNESS

(71) Applicant: Vision Service Plan, Rancho Cordova, CA (US)

(72) Inventors: Jay William Sales, Citrus Heights, CA (US); Richard Chester Klosinski, Jr., Sacramento, CA (US); Matthew Allen Workman, Sacramento, CA (US)

(73) Assignee: Vision Service Plan, Rancho Cordova, CA (US)

( * ) Notice: Subject to any disclaimer, the term of this patent is extended or adjusted under 35 U.S.C. 154(b) by 338 days.

This patent is subject to a terminal disclaimer.

(21) Appl. No.: 15/611,574

(22) Filed: Jun. 1, 2017

(65) Prior Publication Data

US 2017/0265798 A1    Sep. 21, 2017

Related U.S. Application Data

(63) Continuation-in-part of application No. 14/610,439, filed on Jan. 30, 2015, now Pat. No. 10,307,085.
(Continued)

(51) Int. Cl.
*A61B 5/00* (2006.01)
*A61B 5/1455* (2006.01)
(Continued)

(52) U.S. Cl.
CPC .............. *A61B 5/18* (2013.01); *A61B 5/0022* (2013.01); *A61B 5/0077* (2013.01);
(Continued)

(58) Field of Classification Search
CPC ..... A61B 5/1455; A61B 5/112; A61B 5/6803; A61B 5/165; A61B 5/4076; A61B 5/486;
(Continued)

(56) References Cited

U.S. PATENT DOCUMENTS

| 3,505,879 A | 4/1970 | Vanderberg |
| 3,548,663 A | 12/1970 | Radin |

(Continued)

FOREIGN PATENT DOCUMENTS

| EP | 2778612 | 12/2017 |
| GB | 2396421 | 6/2004 |

(Continued)

OTHER PUBLICATIONS

Office Action, dated Jan. 11, 2018, from corresponding U.S. Appl. No. 15/074,679.

(Continued)

*Primary Examiner* — Eric F Winakur
(74) *Attorney, Agent, or Firm* — Brient IP Law, LLC

(57) ABSTRACT

A computer system and method is adapted for determining an alertness of a wearer of a computerized wearable device having one or more sensors by receiving a signal from the sensors and determining a baseline heart rate of the wearer. The system monitors the wearer for an elevated heart rate and/or transmits a stimulus to the wearer to produce an elevated heart rate. In response to the elevated heart rate, the system compares the wearer's current heart rate to the wearer's baseline heart rate to determine the wearer's current alertness by calculating the length of time it takes the wearer's current heart rate to return to the baseline heart rate. The system notifies the wearer of the wearer's current alertness by generating an alert such as sending a notification to the wearer's computing device. The system may also generate an alert from a vehicle driven by the wearer.

18 Claims, 4 Drawing Sheets

Related U.S. Application Data

(60) Provisional application No. 62/046,406, filed on Sep. 5, 2014.

(51) Int. Cl.

| | | |
|---|---|---|
| *A61B 5/16* | (2006.01) | |
| *A61B 5/11* | (2006.01) | |
| *A61B 5/02* | (2006.01) | |
| *A61B 5/18* | (2006.01) | |
| *A61B 5/0205* | (2006.01) | |
| *A61B 5/024* | (2006.01) | |
| *G06F 19/00* | (2018.01) | |
| *G02C 11/00* | (2006.01) | |
| *A61B 7/04* | (2006.01) | |
| *G16H 50/20* | (2018.01) | |
| *G16H 40/63* | (2018.01) | |
| *G06K 9/00* | (2006.01) | |
| *G08B 21/06* | (2006.01) | |
| *A61F 2/76* | (2006.01) | |

(52) U.S. Cl.
CPC ........ *A61B 5/0205* (2013.01); *A61B 5/02438* (2013.01); *A61B 5/6803* (2013.01); *A61B 7/04* (2013.01); *G02C 11/10* (2013.01); *G06F 19/3481* (2013.01); *G06K 9/00684* (2013.01); *G06K 9/00885* (2013.01); *G08B 21/06* (2013.01); *G16H 40/63* (2018.01); *G16H 50/20* (2018.01); *A61B 5/1114* (2013.01); *A61B 5/7282* (2013.01); *A61B 2503/22* (2013.01); *A61F 2/76* (2013.01); *B60Y 2302/07* (2013.01)

(58) Field of Classification Search
CPC ... A61B 5/4884; A61B 5/7246; A61B 5/7278; A61B 5/1116; A61B 5/14552
See application file for complete search history.

(56) References Cited

U.S. PATENT DOCUMENTS

| | | | |
|---|---|---|---|
| 3,972,038 | A | 7/1976 | Fletcher et al. |
| 4,100,401 | A | 7/1978 | Tutt et al. |
| 4,186,609 | A | 2/1980 | Baermann |
| 4,195,642 | A | 4/1980 | Price et al. |
| 4,281,663 | A | 8/1981 | Pringle |
| 4,407,295 | A | 10/1983 | Steuer et al. |
| 4,434,801 | A | 3/1984 | Jiminez et al. |
| 4,855,942 | A | 8/1989 | Bianco |
| 4,878,749 | A | 11/1989 | McGee |
| 4,919,530 | A | 4/1990 | Hyman |
| 5,422,816 | A | 6/1995 | Sprague et al. |
| 5,452,480 | A | 9/1995 | Ryden |
| 5,497,143 | A | 3/1996 | Matsuo et al. |
| 5,585,871 | A | 12/1996 | Linden |
| 5,670,872 | A | 9/1997 | Van De Walle et al. |
| 5,746,501 | A | 5/1998 | Chien et al. |
| 5,891,042 | A | 4/1999 | Sham et al. |
| 5,931,764 | A | 8/1999 | Freeman et al. |
| 5,966,680 | A | 10/1999 | Butnaru |
| 5,976,083 | A | 11/1999 | Richardson et al. |
| 6,013,007 | A | 1/2000 | Root et al. |
| 6,183,425 | B1 | 2/2001 | Whalen et al. |
| 6,218,958 | B1 | 4/2001 | Eichstaedt et al. |
| 6,241,684 | B1 | 6/2001 | Amano et al. |
| 6,325,507 | B1 | 12/2001 | Jannard et al. |
| 6,381,482 | B1 | 4/2002 | Jayaraman et al. |
| 6,431,705 | B1 | 8/2002 | Linden et al. |
| 6,439,067 | B1 | 8/2002 | Goldman et al. |
| 6,513,532 | B2 | 2/2003 | Mault et al. |
| 6,532,298 | B1 | 3/2003 | Cambier et al. |
| 6,736,759 | B1 | 5/2004 | Stubbs et al. |
| 6,769,767 | B2 | 8/2004 | Swab et al. |
| 6,783,501 | B2 | 8/2004 | Takahashi et al. |
| 6,790,178 | B1 | 9/2004 | Mault et al. |
| 6,812,845 | B2 | 11/2004 | Yuzuki et al. |
| 7,181,345 | B2 | 2/2007 | Rosenfeld et al. |
| 7,187,960 | B2 | 3/2007 | Abreu |
| 7,192,136 | B2 | 3/2007 | Howell et al. |
| 7,255,437 | B2 | 8/2007 | Howell et al. |
| 7,376,238 | B1 | 5/2008 | Rivas et al. |
| 7,380,936 | B2 | 6/2008 | Howell et al. |
| 7,400,257 | B2 | 7/2008 | Rivas |
| 7,401,918 | B2 | 7/2008 | Howell et al. |
| 7,438,410 | B1 | 10/2008 | Howell et al. |
| 7,454,002 | B1 | 11/2008 | Gardner et al. |
| 7,457,434 | B2 | 11/2008 | Azar |
| 7,481,531 | B2 | 1/2009 | Howell et al. |
| 7,488,294 | B2 | 2/2009 | Torch |
| 7,500,746 | B1 | 3/2009 | Howell et al. |
| 7,500,747 | B2 | 3/2009 | Howell et al. |
| 7,515,054 | B2 | 4/2009 | Torch |
| 7,543,934 | B2 | 6/2009 | Howell et al. |
| 7,581,833 | B2 | 9/2009 | Howell et al. |
| 7,621,634 | B2 | 11/2009 | Howell et al. |
| 7,630,524 | B2 | 12/2009 | Lauper et al. |
| 7,634,379 | B2 | 12/2009 | Noble |
| 7,640,135 | B2 | 12/2009 | Vock et al. |
| 7,648,463 | B1 | 1/2010 | Elhag et al. |
| 7,677,723 | B2 | 3/2010 | Howell et al. |
| 7,771,046 | B2 | 8/2010 | Howell et al. |
| 7,792,552 | B2 | 9/2010 | Thomas et al. |
| 7,793,361 | B2 | 9/2010 | Ishihara et al. |
| 7,857,772 | B2 | 9/2010 | Bouvier et al. |
| 7,806,525 | B2 | 10/2010 | Howell et al. |
| 7,922,321 | B2 | 4/2011 | Howell et al. |
| 7,987,070 | B2 | 7/2011 | Kahn et al. |
| 8,007,450 | B2 | 8/2011 | Williams |
| 8,011,242 | B2 | 9/2011 | O'Neill et al. |
| 8,081,082 | B2 | 12/2011 | Malik et al. |
| 8,109,629 | B2 | 2/2012 | Howell et al. |
| 8,157,730 | B2 | 4/2012 | Leboeuf et al. |
| 8,188,868 | B2 | 5/2012 | Case |
| 8,202,148 | B2 | 6/2012 | Young |
| 8,294,581 | B2 | 10/2012 | Kamen |
| 8,303,311 | B2 | 11/2012 | Forest |
| 8,337,013 | B2 | 12/2012 | Howell et al. |
| 8,384,617 | B2 | 2/2013 | Braun et al. |
| 8,430,507 | B2 | 4/2013 | Howell et al. |
| 8,448,846 | B2 | 5/2013 | Needham et al. |
| 8,449,471 | B2 | 5/2013 | Tran |
| 8,465,151 | B2 | 6/2013 | Howell et al. |
| 8,494,507 | B1 | 7/2013 | Tedesco et al. |
| 8,500,271 | B2 | 8/2013 | Howell et al. |
| 8,510,166 | B2 | 8/2013 | Neven |
| 8,531,355 | B2 | 9/2013 | Maltz |
| 8,540,583 | B2 | 9/2013 | Leech |
| 8,568,313 | B2 | 10/2013 | Sadhu |
| 8,594,971 | B2 | 11/2013 | Keal et al. |
| 8,620,600 | B2 | 12/2013 | Vock et al. |
| 8,630,633 | B1 | 1/2014 | Tedesco et al. |
| 8,634,701 | B2 | 1/2014 | Kang et al. |
| 8,647,270 | B2 | 2/2014 | Leboeuf et al. |
| 8,690,750 | B2 | 4/2014 | Krueger |
| 8,696,113 | B2 | 4/2014 | Lewis |
| 8,733,928 | B1 | 5/2014 | Lewis |
| 8,750,971 | B2 | 6/2014 | Tran |
| 8,764,651 | B2 | 7/2014 | Tran |
| 8,849,610 | B2 | 9/2014 | Molettiere et al. |
| 8,892,401 | B2 | 11/2014 | Yuen et al. |
| 8,905,542 | B2 | 12/2014 | Howell et al. |
| 8,911,087 | B2 | 12/2014 | Publicover et al. |
| 8,920,332 | B2 | 12/2014 | Hong et al. |
| 8,931,896 | B2 | 1/2015 | Blum et al. |
| 8,941,560 | B2 | 1/2015 | Wong et al. |
| 8,944,590 | B2 | 2/2015 | Blum et al. |
| 8,961,415 | B2 | 2/2015 | Leboeuf et al. |
| 8,964,298 | B2 | 2/2015 | Haddick et al. |
| 8,965,730 | B2 | 2/2015 | Yuen |
| 8,979,295 | B2 | 3/2015 | Waters |
| 9,001,427 | B2 | 4/2015 | Jacobs et al. |
| 9,005,129 | B2 | 4/2015 | Venkatraman et al. |

(56) References Cited

U.S. PATENT DOCUMENTS

| | | |
|---|---|---|
| 9,007,220 B2 | 4/2015 | Johns et al. |
| 9,028,405 B2 | 5/2015 | Tran |
| 9,031,812 B2 | 5/2015 | Roberts et al. |
| 9,033,493 B2 | 5/2015 | Howell et al. |
| 9,035,970 B2 | 5/2015 | Lamb et al. |
| 9,050,033 B2 | 6/2015 | Yoneyama et al. |
| 9,064,342 B2 | 6/2015 | Yuen et al. |
| 9,112,701 B2 | 8/2015 | Sano et al. |
| 9,113,794 B2 | 8/2015 | Hong et al. |
| 9,113,795 B2 | 8/2015 | Hong et al. |
| 9,141,194 B1 | 9/2015 | Keyes et al. |
| 9,144,405 B2 | 9/2015 | Kim et al. |
| 9,153,074 B2 | 10/2015 | Zhou et al. |
| 9,215,290 B2 | 12/2015 | Yuen et al. |
| 9,229,227 B2 | 1/2016 | Border et al. |
| 9,235,064 B2 | 1/2016 | Lewis |
| 9,239,473 B2 | 1/2016 | Lewis |
| 9,241,635 B2 | 1/2016 | Yuen et al. |
| 9,244,293 B2 | 1/2016 | Lewis |
| 9,247,212 B2 | 1/2016 | Bose et al. |
| 9,254,100 B2 | 2/2016 | Beck et al. |
| 9,256,711 B2 | 2/2016 | Horseman |
| 9,304,331 B2 | 4/2016 | Carrara |
| 9,341,526 B2 | 5/2016 | Bass et al. |
| 9,342,610 B2 | 5/2016 | Liu et al. |
| 9,480,877 B2 | 11/2016 | Chiang et al. |
| 9,520,638 B2 | 12/2016 | Baringer et al. |
| 9,529,197 B2 | 12/2016 | Olsson et al. |
| 9,566,033 B2 | 2/2017 | Bogdanovich et al. |
| 9,579,060 B1 | 2/2017 | Lisy et al. |
| 9,610,476 B1 | 4/2017 | Tran et al. |
| 9,726,904 B1 | 8/2017 | Lin |
| 9,763,592 B2 | 9/2017 | Le et al. |
| 9,896,154 B2 | 2/2018 | Modolo |
| 9,977,259 B2 | 5/2018 | Archambeau et al. |
| 10,188,323 B2 | 1/2019 | Sales et al. |
| 10,310,296 B2 | 6/2019 | Howell et al. |
| 10,330,956 B2 | 6/2019 | Howell et al. |
| 2001/0031031 A1 | 10/2001 | Ogawa et al. |
| 2002/0151810 A1 | 10/2002 | Wong et al. |
| 2003/0195398 A1 | 10/2003 | Suzuki et al. |
| 2004/0039517 A1 | 2/2004 | Biesinger et al. |
| 2005/0033200 A1 | 2/2005 | Soehren et al. |
| 2005/0036103 A1 | 2/2005 | Bloch |
| 2005/0054942 A1 | 3/2005 | Melker et al. |
| 2006/0115130 A1 | 6/2006 | Kozlay |
| 2007/0052672 A1 | 3/2007 | Ritter et al. |
| 2007/0112287 A1 | 5/2007 | Fancourt et al. |
| 2007/0273611 A1 | 11/2007 | Torch |
| 2008/0137916 A1 | 6/2008 | Lauber et al. |
| 2009/0030350 A1 | 1/2009 | Yang et al. |
| 2009/0195747 A1 | 8/2009 | Insua |
| 2009/0227853 A1 | 9/2009 | Wijesiriwardana |
| 2009/0267805 A1 | 10/2009 | Jin et al. |
| 2010/0042430 A1 | 2/2010 | Bartfeld |
| 2010/0045928 A1 | 2/2010 | Levy |
| 2010/0110368 A1 | 5/2010 | Chaum |
| 2010/0136508 A1 | 6/2010 | Zekhtser |
| 2010/0271587 A1 | 10/2010 | Pavlopoulos |
| 2010/0280336 A1 | 11/2010 | Giftakis et al. |
| 2010/0308999 A1 | 12/2010 | Chornenky |
| 2010/0332571 A1 | 12/2010 | Healey et al. |
| 2011/0169932 A1 | 7/2011 | Mula et al. |
| 2011/0221656 A1 | 9/2011 | Haddick et al. |
| 2011/0224505 A1 | 9/2011 | Sadhu |
| 2012/0021806 A1 | 1/2012 | Maltz |
| 2012/0029367 A1 | 2/2012 | Hobeika |
| 2012/0127423 A1 | 5/2012 | Blum et al. |
| 2012/0133885 A1 | 5/2012 | Howell et al. |
| 2012/0135384 A1 | 5/2012 | Nakao |
| 2012/0142443 A1 | 6/2012 | Savarese et al. |
| 2012/0169990 A1 | 7/2012 | Burnstein |
| 2012/0191016 A1 | 7/2012 | Jastram |
| 2012/0203310 A1 | 8/2012 | Pugh et al. |
| 2012/0206485 A1 | 8/2012 | Osterhout et al. |
| 2012/0310442 A1 | 12/2012 | Doutaz et al. |
| 2013/0009907 A1 | 1/2013 | Rosenberg et al. |
| 2013/0009993 A1* | 1/2013 | Horseman ............ G16H 40/63 345/633 |
| 2013/0024022 A1 | 1/2013 | Bowers |
| 2013/0024211 A1 | 1/2013 | Monteforte et al. |
| 2013/0041590 A1 | 2/2013 | Burich et al. |
| 2013/0050258 A1 | 2/2013 | Liu et al. |
| 2013/0096397 A1 | 4/2013 | Kiso et al. |
| 2013/0138413 A1 | 5/2013 | Finch et al. |
| 2013/0157232 A1 | 6/2013 | Ehrenkranz |
| 2013/0242262 A1 | 9/2013 | Lewis |
| 2013/0274587 A1 | 10/2013 | Coza et al. |
| 2013/0274904 A1 | 10/2013 | Coza et al. |
| 2013/0307670 A1 | 11/2013 | Ramaci |
| 2013/0329183 A1 | 12/2013 | Blum et al. |
| 2013/0345168 A1 | 12/2013 | Kim et al. |
| 2014/0028456 A1 | 1/2014 | Sadhu |
| 2014/0031703 A1 | 1/2014 | Rayner et al. |
| 2014/0063242 A1 | 3/2014 | Hanina et al. |
| 2014/0073081 A1 | 3/2014 | Wang |
| 2014/0078049 A1 | 3/2014 | Parshionikar |
| 2014/0085190 A1 | 3/2014 | Erinjippurath et al. |
| 2014/0135593 A1 | 5/2014 | Jayalth et al. |
| 2014/0142459 A1 | 5/2014 | Jayalth et al. |
| 2014/0159862 A1 | 6/2014 | Yang et al. |
| 2014/0204334 A1 | 7/2014 | Stoll |
| 2014/0207264 A1 | 7/2014 | Quy |
| 2014/0218281 A1 | 8/2014 | Amayeh et al. |
| 2014/0228649 A1 | 8/2014 | Rayner et al. |
| 2014/0229220 A1 | 8/2014 | Yuen et al. |
| 2014/0247145 A1 | 9/2014 | Proud |
| 2014/0266988 A1 | 9/2014 | Fisher et al. |
| 2014/0276096 A1 | 9/2014 | Bonutti |
| 2014/0340221 A1 | 11/2014 | Yuen et al. |
| 2014/0346158 A1 | 11/2014 | Matthews |
| 2014/0375452 A1 | 12/2014 | Yuen et al. |
| 2014/0375470 A1 | 12/2014 | Malveaux |
| 2014/0378872 A1 | 12/2014 | Hong et al. |
| 2015/0057512 A1 | 2/2015 | Kapoor |
| 2015/0085245 A1 | 3/2015 | Howell et al. |
| 2015/0088464 A1 | 3/2015 | Yuen et al. |
| 2015/0173631 A1 | 6/2015 | Richards et al. |
| 2015/0179050 A1 | 6/2015 | Katingari et al. |
| 2015/0185506 A1 | 7/2015 | Lewis |
| 2015/0212329 A1 | 7/2015 | Sugihara et al. |
| 2015/0223805 A1 | 8/2015 | Whitman et al. |
| 2015/0244910 A1 | 8/2015 | Marston et al. |
| 2015/0281879 A1 | 10/2015 | Saadi et al. |
| 2015/0287338 A1 | 10/2015 | Wells et al. |
| 2015/0332149 A1 | 11/2015 | Kolb et al. |
| 2015/0342482 A1 | 12/2015 | Carrara |
| 2015/0366518 A1 | 12/2015 | Sampson |
| 2016/0007849 A1 | 1/2016 | Krueger |
| 2016/0034042 A1 | 2/2016 | Joo |
| 2016/0041404 A1 | 2/2016 | Palermo et al. |
| 2016/0041613 A1 | 2/2016 | Klanner et al. |
| 2016/0117937 A1 | 4/2016 | Penders et al. |
| 2016/0314468 A1 | 10/2016 | Smith et al. |
| 2017/0071528 A1 | 3/2017 | Chen |
| 2017/0323584 A1 | 11/2017 | Daniel et al. |

FOREIGN PATENT DOCUMENTS

| | | |
|---|---|---|
| WO | 2005015163 | 2/2005 |
| WO | 2005094667 | 10/2005 |
| WO | 2007088374 | 8/2007 |
| WO | 2008073806 | 6/2008 |
| WO | 2010006370 | 1/2010 |
| WO | 2010062479 | 6/2010 |
| WO | 2010062481 | 6/2010 |
| WO | 2011086466 | 7/2011 |
| WO | 2012041485 | 4/2012 |
| WO | 2013188343 | 12/2013 |
| WO | 2014021602 | 2/2014 |
| WO | 2014108481 | 7/2014 |
| WO | 2014144918 | 9/2014 |
| WO | 2014144940 | 9/2014 |
| WO | 2014170280 | 10/2014 |

(56) References Cited

FOREIGN PATENT DOCUMENTS

| WO | 2014188244 | 11/2014 |
|---|---|---|
| WO | 2015015025 | 2/2015 |
| WO | 2015081299 | 6/2015 |
| WO | 2015095924 | 7/2015 |
| WO | 2015127143 | 8/2015 |
| WO | 2015127441 | 8/2015 |
| WO | 2016017997 | 2/2016 |
| WO | 2016029803 | 3/2016 |

OTHER PUBLICATIONS

Office Action, dated Sep. 29, 2017, from corresponding U.S. Appl. No. 14/506,249.
Restriction Requirement, dated Oct. 4, 2017, from corresponding U.S. Appl. No. 14/610,439.
Office Action, dated Sep. 26, 2017, from corresponding U.S. Appl. No. 14/846,401.
Restriction Requirement, dated Sep. 13, 2017, from corresponding U.S. Appl. No. 14/550,406.
Notice of Allowance, dated Oct. 20, 2017, from corresponding U.S. Appl. No. 15/489,147.
Final Office Action, dated Nov. 16, 2017, from corresponding U.S. Appl. No. 14/610,628.
Office Action, dated Nov. 30, 2017, from corresponding U.S. Appl. No. 14/550,406.
Jeannet, Pierre-Yves, et al., "Continuous monitoring and quantification of multiple parameters of daily physical activity in ambulatory Duchenne muscular, dystrophy patients", Official Journal of the European Paediatric Neurology Society, 2011.
Notice of Allowance, dated Dec. 13, 2017, from corresponding U.S. Appl. No. 14/610,501.
Notice of Allowance, dated Jun. 5, 2019, from corresponding U.S. Appl. No. 14/550,406.
Office Action, dated Jun. 11, 2019, from corresponding U.S. Appl. No. 14/610,501.
Office Action, dated Jun. 27, 2019, from corresponding U.S. Appl. No. 15/060,333.
Notice of Allowance, dated Oct. 11, 2018, from corresponding U.S. Appl. No. 15/074,679.
Final Office Action, dated Dec. 11, 2018, from corresponding U.S. Appl. No. 14/610,501.
Final Office Action, dated Dec. 31, 2018, from corresponding U.S. Appl. No. 14/550,406.
Final Office Action, dated Dec. 15, 2016, from corresponding U.S. Appl. No. 14/506,249.
Final Office Action, dated Sep. 26, 2016, from corresponding U.S. Appl. No. 14/610,628.
International Search Report, dated Dec. 18, 2015, from corresponding International Application No. PCT/US2015/048662.
International Search Report, dated Jan. 21, 2016, from corresponding International Application No. PCT/US2015/048612.
International Search Report, dated Jan. 21, 2016, from corresponding International Application No. PCT/US2015/048656.
International Search Report, dated Jun. 2, 2016, from corresponding International Application No. PCT/US2016/015705.
Invitation to Pay Additional Search Fees, dated Apr. 1, 2016, from corresponding International Application Serial No. PCT/US2016/015705.
Invitation to Pay Additional Search Fees, dated Nov. 4, 2015, from corresponding International Application Serial No. PCT/US2015/048612.
Invitation to Pay Additional Search Fees, dated Nov. 4, 2015, from corresponding International Application Serial No. PCT/US2015/048656.
Maria S. Redin, "Marathon Man", Article Jun. 15, 1998, MIT Media Laboratory.
Office Action, dated Aug. 19, 2016, from corresponding U.S. Appl. No. 14/578,039.
Office Action, dated Jul. 1, 2016, from corresponding U.S. Appl. No. 14/562,454.
Office Action, dated Jul. 22, 2016, from corresponding U.S. Appl. No. 14/506,249.
Office Action, dated Sep. 2, 2016, from corresponding U.S. Appl. No. 14/588,122.
Restriction Requirement, dated Nov. 10, 2016, from corresponding U.S. Appl. No. 14/846,401.
Richard M. Satava, et al., "The Physiologic Cipher at Altitude: Telemedicine and Real-Time Monitoring of Climbers on Mount Everest", Telemedicine Journal and e-Health, vol. 6, No. 3, 2000, Mary Ann Liebert, Inc.
Written Opinion of the International Searching Authority, dated Dec. 18, 2015, from corresponding International Application No. PCT/US2015/048662.
Written Opinion of the International Searching Authority, dated Jan. 21, 2016, from corresponding International Application No. PCT/US2015/048612.
Written Opinion of the International Searching Authority, dated Jan. 21, 2016, from corresponding International Application No. PCT/US2015/048656.
Written Opinion of the International Searching Authority, dated Jun. 2, 2016, from corresponding International Application No. PCT/US2016/015705.
Office Action, dated Dec. 29, 2016, from corresponding U.S. Appl. No. 14/610,589.
Phend, Crystal, "Calorie Intake Rises as Sleep Time Drops," Medpage Today, Medpage Today, LLC, Mar. 15, 2012, Web Dec. 19, 2016, http://www.medpagetoday.com/cardiology/prevention/31663.
Michael Franco, Tzoa wearable turns you into a walking air-quality sensor, Dec. 9, 2014, CNET, https://www.cnet.com/news/tzoa-wearable-turns-you-into-a-walking-air-quality-sensor/.
Notice of Allowance, dated Feb. 28, 2017, from corresponding U.S. Appl. No. 14/588,122.
Office Action, dated Feb. 10, 2017, from corresponding U.S. Appl. No. 14/846,401.
Office Action, dated Mar. 3, 2017, from corresponding U.S. Appl. No. 14/610,628.
Office Action, dated Mar. 8, 2016, from corresponding U.S. Appl. No. 14/610,628.
Ted Burnham, Wearable Air Quality Sensor: Tzoa, Jan. 5, 2015, Postscapes, http://www.postscapes.com/wearable-air-quality-sensor-tzoa/.
Final Office Action, dated Mar. 29, 2017, from corresponding U.S. Appl. No. 14/562,454.
International Preliminary Report on Patentability, dated Mar. 16, 2017, from corresponding International Application No. PCT/US2015/048612.
International Preliminary Report on Patentability, dated Mar. 16, 2017, from corresponding International Application No. PCT/US2015/048656.
International Preliminary Report on Patentability, dated Mar. 16, 2017, from corresponding International Application No. PCT/US2015/048662.
Notice of Allowance, dated Sep. 13, 2018, from corresponding U.S. Appl. No. 15/594,898.
Office Action, dated Sep. 11, 2018, from corresponding U.S. Appl. No. 15/060,333.
Final Office Action, dated Sep. 25, 2018, from corresponding U.S. Appl. No. 14/610,439.
Office Action, dated Oct. 4, 2018, from corresponding U.S. Appl. No. 15/791,196.
Office Action, dated Mar. 2, 2018, from corresponding U.S. Appl. No. 15/060,333.
Office Action, dated Mar. 9, 2018, from corresponding U.S. Appl. No. 14/610,439.
Final Office Action, dated Mar. 30, 2018, from corresponding U.S. Appl. No. 14/846,401.
Office Action, dated May 23, 2018, from corresponding U.S. Appl. No. 14/578,039.
Final Office Action, dated Jan. 14, 2019, from corresponding U.S. Appl. No. 14/578,039.

(56) References Cited

OTHER PUBLICATIONS

Final Office Action, dated Jan. 14, 2019, from corresponding U.S. Appl. No. 15/060,333.
Notice of Allowance, dated Jan. 17, 2019, from corresponding U.S. Appl. No. 14/610,439.
Office Action, dated Jun. 8, 2018, from corresponding U.S. Appl. No. 14/610,501.
Final Office Action, dated Jun. 14, 2018, from corresponding U.S. Appl. No. 15/074,679.
Office Action, dated Aug. 7, 2018, from corresponding U.S. Appl. No. 14/550,406.
Office Action, dated Feb. 11, 2019, from corresponding U.S. Appl. No. 14/846,401.
Office Action, dated Apr. 4, 2019, from corresponding U.S. Appl. No. 16/284,615.
Office Action, dated Mar. 21, 2019, from corresponding U.S. Appl. No. 16/259,646.
Final Office Action, dated Apr. 29, 2019, from corresponding U.S. Appl. No. 15/791,196.
Final Office Action, dated Jun. 30, 2017, from corresponding U.S. Appl. No. 14/610,589.
Shankland, Stephen, "Google's electronic eyewear get 'OK Glass' voice commands", Feb. 20, 2013, Cnet.com, https://www.cnet.com/news/googles-electronic-eyewear-gets-ok-glass-voice-commands/.
Office Action, dated Jun. 29, 2017, from corresponding U.S. Appl. No. 15/489,147.
Final Office Action, dated Jul. 10, 2017, from corresponding U.S. Appl. No. 14/846,401.
Final Office Action, dated May 23, 2017, from corresponding U.S. Appl. No. 14/578,039.
Notice of Allowance, dated Jun. 21, 2017, from corresponding U.S. Appl. No. 14/562,454.
Office Action, dated Jun. 27, 2017, from corresponding U.S. Appl. No. 15/060,333.
Tolentino, Mellisa, Udderly Clever Wearable Tech Solutions, http://siliconangle.com/blog/2014/03/25/udderly-clever-wearable-tech-solutions/, Mar. 25, 2014.
Torres, Juan Carlos, ODG R-7 Smart Glasses Carries Its Own Android Inside, http://androidcommunity.com/bdg-r-7-smart-glasses-carries-its-own-android-inside-20140919/, Sep. 19, 2014.
Final Office Action, dated Jul. 18, 2019, from corresponding U.S. Appl. No. 14/846,401.
Office Action, dated Jul. 26, 2019, from corresponding U.S. Appl. No. 16/259,646.
Notice of Allowance, dated Jul. 31, 2019, from corresponding U.S. Appl. No. 16/284,615.
Office Action, dated Aug. 6, 2019, from corresponding U.S. Appl. No. 16/429,480.
Office Action, dated Oct. 4, 2019, from corresponding U.S. Appl. No. 15/191,196.
Notice of Allowance, dated Sep. 11, 2019, from corresponding U.S. Appl. No. 16/259,646.

\* cited by examiner

US 10,617,342 B2

SYSTEMS, APPARATUS, AND METHODS FOR USING A WEARABLE DEVICE TO MONITOR OPERATOR ALERTNESS

CROSS-REFERENCE TO RELATED APPLICATION

This application is a continuation-in-part of U.S. Provisional patent application Ser. No. 14/610,439, filed Jan. 30, 2015, and entitled, "Wearable Physiology Monitor Computer Apparatus, Systems, and Related Methods," which claims the benefit of U.S. Provisional Patent Application No. 62/046,406, filed Sep. 5, 2014, and entitled, "Wearable Health Computer Apparatus, Systems, and Related Methods," the disclosures of which are hereby incorporated by reference herein in their entirety.

BACKGROUND

Individuals may become drowsy while driving or operating a machine because of monotonous driving conditions, lack of sleep, or due to a medical condition. When individuals drive or operate machinery while drowsy, accidents are prone to happen. Other accidents may also occur when an individual becomes distracted while driving or operating machinery. Accordingly, there is a need for improved systems and methods for monitoring the alertness of an individual, especially when the individual is driving or operating machinery. Various embodiments of the present systems and methods recognize and address the foregoing considerations, and others, of prior art systems and methods.

SUMMARY OF THE VARIOUS EMBODIMENTS

In general, in various embodiments, a computer-implemented method is adapted for determining the alertness of a wearer of a computerized wearable device. The computerized wearable device comprises one or more sensors coupled to the computerized wearable device. The one or more sensors are adapted to detect one or more physiological characteristics of the wearer of the computerized wearable device, where the one or more characteristics are associated with the wearer's alertness. The computerized wearable device also comprises one or more stimulus transmitters coupled to the computerized wearable device, where the one or more stimulus transmitters are adapted to initiate the transmission of one or more stimuli to the wearer. The method comprises: (1) receiving, by a processor, at least one signal from the one or more sensors of the computerized wearable device; (2) at least partially in response to receiving the at least one signal, determining, by a processor, a baseline heart rate of the wearer of the computerized wearable device; (3) transmitting, by a processor, at least one stimulus from the one or more stimulus transmitters to the wearer; (4) determining, by a processor, a current heart rate of the wearer; (5) comparing, by a processor, the current heart rate of the wearer to the baseline heart rate of the wearer; (6) at least partially in response to comparing the current heart rate of the wearer to the baseline heart rate of the wearer, determining, by a processor, the current alertness level of the wearer; and (7) notifying, by a processor, the wearer of the wearer's current alertness level.

In general, in various embodiments, a computer system is adapted for determining the alertness of a wearer of a computerized wearable device comprising one or more sensors coupled to the computerized wearable device. The one or more sensors are adapted to detect one or more physiological characteristics of the wearer of the computerized wearable device, where the one or more characteristics are associated with the wearer's alertness. The computer system comprises at least one processor, where the computer system is configured for: (1) receiving at least one signal from the one or more sensors of the computerized wearable device; (2) at least partially in response to receiving the at least one signal, measuring one or more baseline heart rates of the wearer of the computerized wearable device that are indicative of a normal heart rate of the wearer; (3) receiving a current heart rate of the wearer; (4) determining that the current heart rate of the wearer is above a predetermined heart rate threshold value that corresponds to an excited state of the wearer; (5) calculating a length of time that the current heart rate of the wearer remains above the predetermined heart rate threshold value; (6) comparing the current heart rate of the wearer to the normal heart rate of the wearer; (7) at least partially in response to comparing the current heart rate of the wearer to the normal heart rate of the wearer, determining the current alertness level of the wearer; and (8) notifying the wearer of the wearer's current alertness level.

In general, in various embodiments, a computerized eyewear comprises at least one processor and one or more sensors operatively coupled to the at least one processor. The one or more sensors are selected from a group consisting of: (1) a heart rate monitor; (2) a pulse oximeter; (3) a gyroscope; (4) a forward facing camera; and (5) an eye-facing camera. The computerized eyewear further comprises a power source operatively coupled to the at least one processor a communication device operatively coupled to the at least one processor. The computerized eyewear is configured to: (1) receive at least one signal from the one or more sensors on the computerized wearable device; (2) at least partially in response to receiving the at least one signal, determine a current alertness of the wearer of the computerized eyewear; (3) at least partially in response to determining the current alertness of the wearer, compare the current alertness of the wearer to a normal alertness of the wearer; and (4) notify the wearer when the current alertness of the wearer deviates from the normal alertness of the wearer.

BRIEF DESCRIPTION OF THE DRAWINGS

Various embodiments of systems and methods for detecting attributes a wearer's physiology are described below. In the course of this description, reference will be made to the accompanying drawings, which are not necessarily drawn to scale and wherein.

DETAILED DESCRIPTION OF SOME EMBODIMENTS

Figure 1:
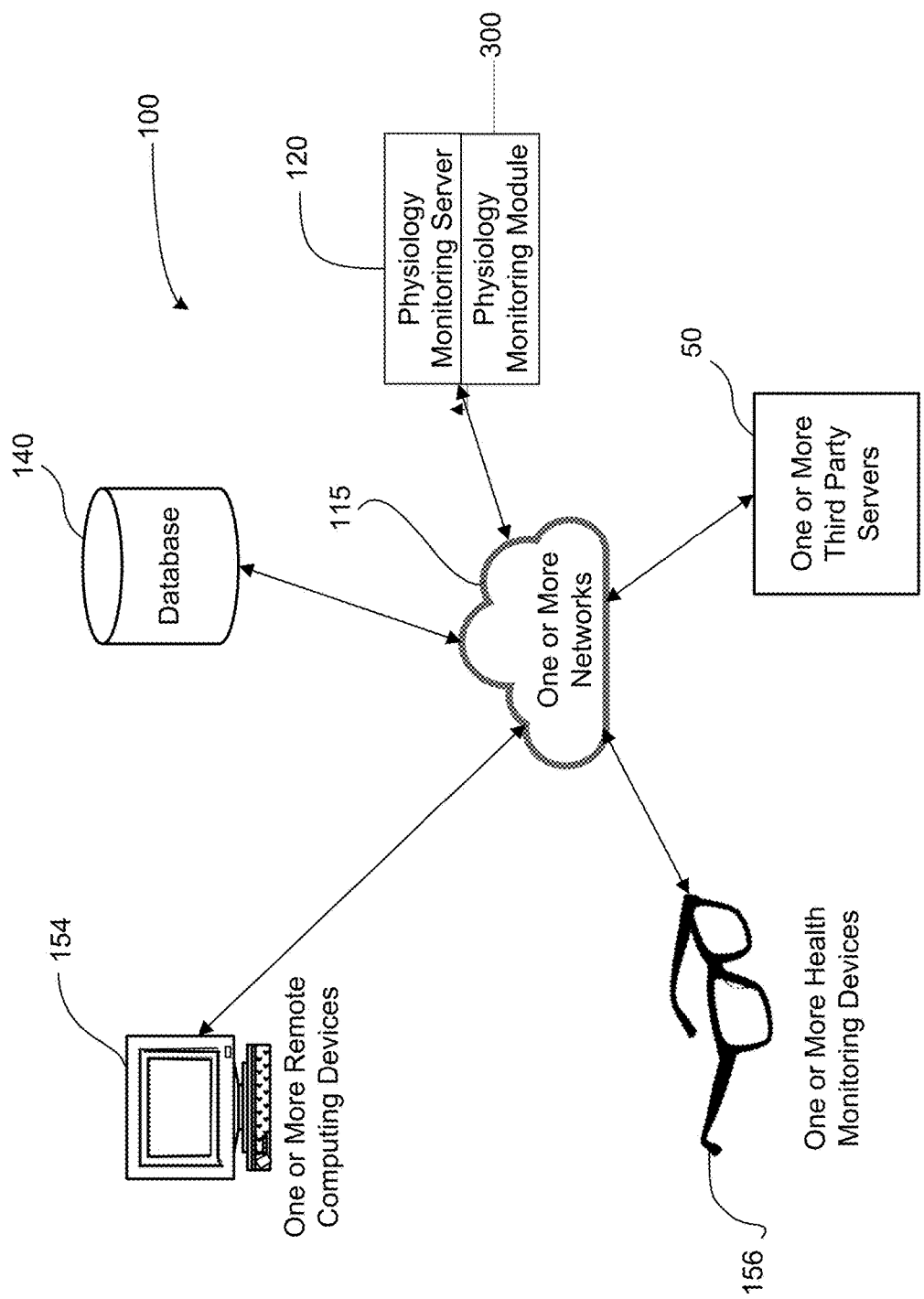
FIG. 1 is a block diagram of an Alertness Monitoring System in accordance with an embodiment of the present system.

Various embodiments will now be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

A wearable alertness monitoring system, in various embodiments, may, for example, be embodied in any suitable wearable device configured to monitor the alertness of a wearer. The system may, for example, be embodied as a pair of eyewear, as contact lenses, as a wristwatch, as a suitable piece of clothing (e.g., such as a suitable shirt, pair of pants, undergarment, compression sleeve, etc.), as footwear, as a hat, as a helmet, as an orthopedic cast, or any other suitable wearable item. In a particular example, a wearable alertness monitoring system embodied as a pair of eyewear may enable the system to access one or more (e.g., all five) of a wearer's senses (e.g., touch, sight, sound, smell, and taste) based at least in part on a proximity of the eyewear to the wearer's sensory systems (e.g., eyes, mouth, ears, nose) when worn by the wearer. In other embodiments, a wearable alertness monitoring system embodied as a helmet may enable the system to determine impact, acceleration, posture, and other physiological attributes of the wearer.

In various embodiments, the system comprises one or more sensors configured to determine one or more physiological attributes of the wearer. The one or more sensors may be coupled to the wearable device in any suitable way. For instance, the one or more sensors may be embedded into the wearable device, coupled to the wearable device, and/or operatively coupled to the wearable device. The one or more sensors may include, for example, one or more heart rate monitors, one or more electrocardiogram (EKG) sensors, one or more pedometers, one or more gyroscopes, one or more geomagnetic sensors, one or more thermometers, one or more front-facing cameras, one or more eye-facing cameras, one or more microphones, one or more accelerometers, one or more blood pressure sensors, one or more pulse oximeters, one or more near-field communication sensors, one or more bone scanners, one or more infrared LED/photodiode sensor combinations, one or more photodiode sensors, one or more magnetometers, or any other suitable one or more sensors. In particular embodiments, the system is configured to gather data about the wearer, for example, using the one or more sensors (e.g., such as temperature, balance, heart rate, activity, activity levels, alertness, food eaten, medications taken, steps taken, head position, body movements, facial muscle movements, trauma, etc.).

In some embodiments, one or more body position sensors may be physically or wirelessly coupled to the wearable device and adapted to assess the relative positions of two or more of the wearer's body parts over time in order to determine whether the wearer's head position is desirable or undesirable (e.g., whether the wearer's head has slumped forward). For example, the wearable device may include a magnetometer that is adapted to sense the relative positions of a first magnet that a wearer is wearing adjacent the wearer's forehead (e.g., as an adhesive attachment or embedded within an article of clothing) and a second magnet that the wearer is wearing adjacent the wearer's chest (e.g., as an adhesive attachment or embedded within an article of clothing). The system may then use data obtained from the magnetometer regarding the relative positions of the magnets to determine whether the wearer's head is slumping forward. In response to determining that the wearer's head is slumping forward, the system may send an alert to the wearer indicating that they should resume a correct head position.

In various embodiments, the sensors determine the alertness of the wearer by monitoring the wearer's heart rate, pulse, orientation, acceleration, geomagnetic field, and images from the one or more front facing cameras and/or one or more eye-facing cameras. The system may measure the wearer's baseline levels based on these characteristics to determine the wearer's normal alertness. The system may measure the wearer's baseline once to create a static baseline, or intermittently to create a dynamic baseline. After determining the wearer's normal alertness based on the baseline levels from the sensors, the system may receive at least one signal from the one or more sensors. The system may use the at least one signal received from the one or more sensors to determine the wearer's current alertness. The system may then compare the wearer's current alertness to the wearer's baseline (e.g., normal) alertness. If the wearer's current alertness deviates from the normal alertness of the wearer, the system may notify the wearer of the deviation. In some embodiments, the system may notify a third party of the deviation. In various embodiments, the system may notify the wearer via the wearable device or through a notification sent to a mobile device associated with the wearer. In some embodiments, the system may also provide suggestions to the wearer on how to change the wearer's current alertness to conform to the wearer's normal alertness. The system, in particular embodiments, may also provide suggestions to the wearer on the cause of the wearer's current alertness. For instance, where the wearer's current alertness includes a lowered head, closed eyes, and slumped shoulders (as determined by additional sensors placed on the wearer's shoulders) and the wearer's normal alertness is sitting up straight with shoulders back, the system may determine that the wearer is sleeping. After determining that the wearer is sleeping, the system may notify the wearer to wake up or to correct their current alertness to their normal alertness. The system may also suggest the cause of the wearer's deviation in alertness (e.g., fatigue).

In various embodiments, while the system is using one or more sensors (e.g., eyewear based sensors) to assess the alertness of the wearer, the system may also (e.g., at least substantially simultaneously) capture one or more images of the wearer or the wearer's surroundings (e.g., using a camera, such as a forward-facing camera associated with eyewear worn by the wearer) that may be used in determining the user's activity or physiological state.

Exemplary Technical Platforms

As will be appreciated by one skilled in the relevant field, the present systems and methods may be, for example, embodied as a computer system, a method, or a computer program product. Accordingly, various embodiments may be entirely hardware or a combination of hardware and software. Furthermore, particular embodiments may take the form of a computer program product stored on a computer-readable storage medium having computer-readable instructions (e.g., software) embodied in the storage medium. Various embodiments may also take the form of web-implemented computer software. Any suitable computer-readable storage medium may be utilized including, for example, hard disks, compact disks, DVDs, optical storage devices, and/or magnetic storage devices.

Various embodiments are described below with reference to block diagram and flowchart illustrations of methods, apparatuses, (e.g., systems), and computer program products. It should be understood that each block of the block diagrams and flowchart illustrations, and combinations of blocks in the block diagrams and flowchart illustrations, respectively, can be implemented by a computer executing computer program instructions. These computer program instructions may be loaded onto a general purpose computer, a special purpose computer, or other programmable data processing apparatus that can direct a computer or other programmable data processing apparatus to function in a particular manner such that the instructions stored in the computer-readable memory produce an article of manufacture that is configured for implementing the functions specified in the flowchart block or blocks.

The computer instructions may execute entirely on the user's computer, partly on the user's computer, as a stand-alone software package, partly on a user's computer and partly on a remote computer, or entirely on the remote computer or server. In the latter scenario, the remote computer may be connected to the user's computer through any type of network, including but not limited to: a local area network (LAN); a wide area network (WAN); a cellular network; or the connection may be made to an external computer (for example, through the Internet using an Internet Service Provider).

These computer program instructions may also be stored in a computer-readable memory that can direct a computer or other programmable data processing apparatus to function in a particular manner such that the instructions stored in the computer-readable memory produce an article of manufacture that is configured for implementing the function specified in the flowchart block or blocks. The computer program instructions may also be loaded onto a computer or other programmable data processing apparatus to cause a series of operational steps to be performed on the computer or other programmable apparatus to produce a computer-implemented process (e.g., method) such that the instructions that execute on the computer or other programmable apparatus provide steps for implementing the functions specified in the flowchart block or blocks.

Example System Architecture

FIG. 1 is a block diagram of an Alertness Monitoring System 100 according to particular embodiments. As may be understood from this figure, the Alertness Monitoring System 100 includes One or More Networks 115, One or More Third Party Servers 50, an Alertness Monitoring Server 120 that may, for example, be adapted to execute an Alertness Monitoring Module 300, a Database 140, One or More Remote Computing Devices 154 (e.g., such as a smart phone, a tablet computer, a wearable computing device, a laptop computer, a desktop computer, etc.), and One or More Wearable Health Monitoring Devices 156, which may, for example, be embodied as one or more of eyewear, headwear, clothing, a watch, a hat, a helmet, a cast, an adhesive bandage, a piece of jewelry (e.g., a ring, earring, necklace, bracelet, etc.), or any other suitable wearable device. In particular embodiments, the one or more computer networks 115 facilitate communication between the One or More Third Party Servers 50, the Alertness Monitoring Server 120, Database 140, One or More Remote Computing Devices 154, and the one or more Health Monitoring Devices 156.

The one or more networks 115 may include any of a variety of types of wired or wireless computer networks such as the Internet, a private intranet, a mesh network, a public switch telephone network (PSTN), or any other type of network (e.g., a network that uses Bluetooth or near field communications to facilitate communication between computing devices). The communication link between the One or More Remote Computing Devices 154 and the Mental State Monitoring Server 120 may be, for example, implemented via a Local Area Network (LAN) or via the Internet.

Figure 2:
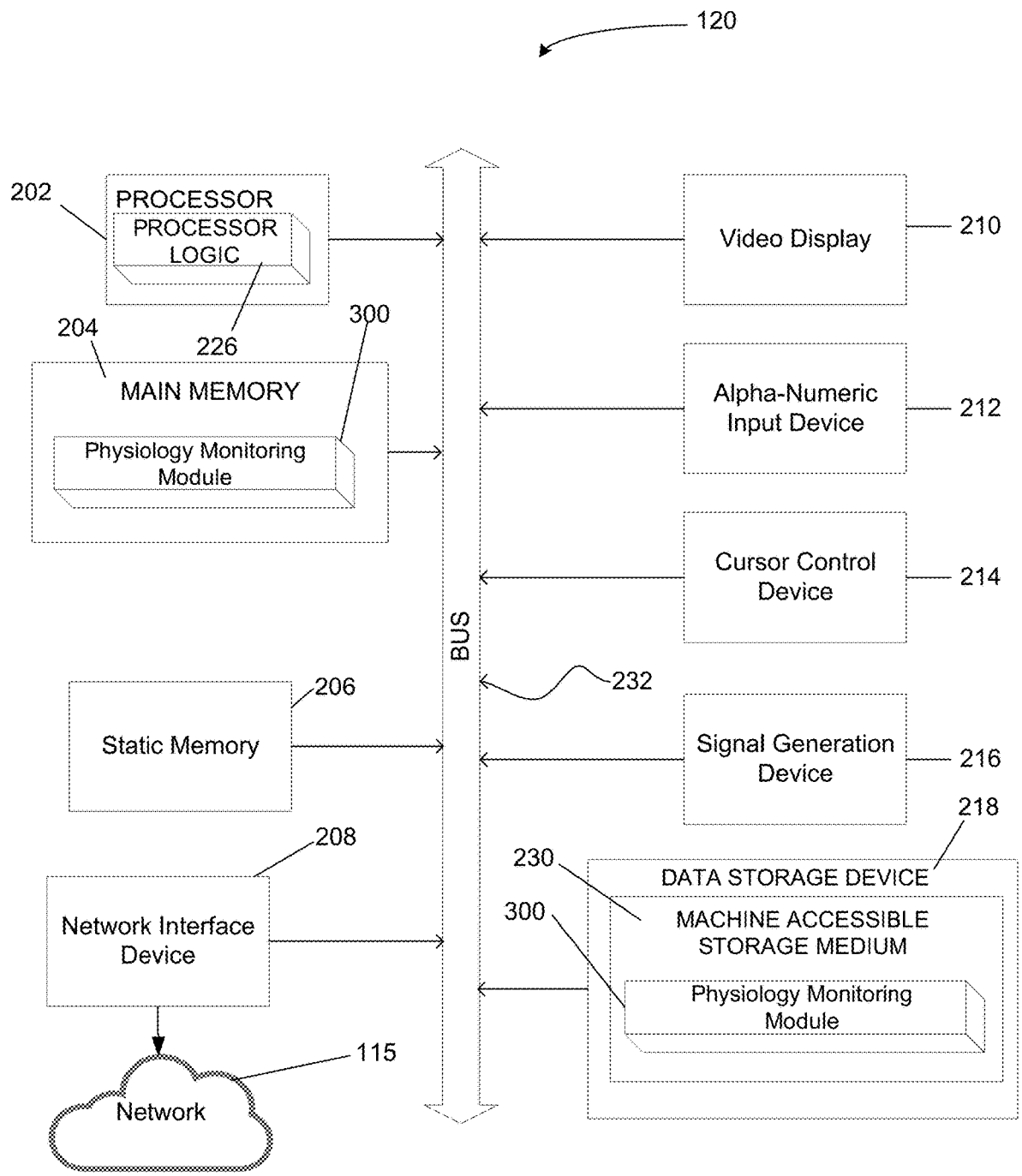
FIG. 2 is a block diagram of the Alertness Monitoring Server of FIG. 1.

FIG. 2 illustrates a diagrammatic representation of the architecture for the Alertness Monitoring Server 120 that may be used within the Alertness Monitoring System 100. It should be understood that the computer architecture shown in FIG. 2 may also represent the computer architecture for any one of the One or More Remote Computing Devices 154, the one or more Third Party Servers 50, and the one or more Health Monitoring Devices 156 shown in FIG. 1. In particular embodiments, the Alertness Monitoring Server 120 may be suitable for use as a computer within the context of the Alertness Monitoring System 100 that is configured for determining an alertness of a wearer of a computerized wearable device using signals received from sensors coupled to the computerized wearable device.

In particular embodiments, the Alertness Monitoring Server 120 may be connected (e.g., networked) to other computing devices in a LAN, an intranet, an extranet, and/or the Internet as shown in FIG. 1. As noted above, the Alertness Monitoring Server 120 may operate in the capacity of a server or a client computing device in a client-server network environment, or as a peer computing device in a peer-to-peer (or distributed) network environment. The Alertness Monitoring Server 120 may be a desktop personal computing device (PC), a tablet PC, a set-top box (STB), a Personal Digital Assistant (PDA), a cellular telephone, a web appliance, a network router, a switch or bridge, or any other computing device capable of executing a set of instructions (sequential or otherwise) that specify actions to be taken by that computing device. Further, while only a single computing device is illustrated, the term "computing device" shall also be interpreted to include any collection of computing devices that individually or jointly execute a set (or multiple sets) of instructions to perform any one or more of the methodologies discussed herein.

An exemplary Alertness Monitoring Server 120 includes a processing device 202, a main memory 204 (e.g., read-only memory (ROM), flash memory, dynamic random access memory (DRAM) such as synchronous DRAM (SDRAM) or Rambus DRAM (RDRAM), etc.), a static memory 206 (e.g., flash memory, static random access memory (SRAM), etc.), and a data storage device 218, which communicate with each other via a bus 232.

The processing device 202 represents one or more general-purpose or specific processing devices such as a microprocessor, a central processing unit (CPU), or the like. More particularly, the processing device 202 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. The processing device 202 may also be one or more special-purpose processing devices such as an application specific integrated circuit (ASIC), a field programmable gate array (FPGA), a digital signal processor (DSP), network processor, or the like. The processing device 202 may be configured to execute processing logic 226 for performing various operations and steps discussed herein.

The Alertness Monitoring Server 120 may further include a network interface device 208. The Alertness Monitoring Server 120 may also include a video display unit 210 (e.g., a liquid crystal display (LCD) or a cathode ray tube (CRT)), an alpha-numeric input device 212 (e.g., a keyboard), a cursor control device 214 (e.g., a mouse), and a signal generation device 216 (e.g., a speaker).

The data storage device 218 may include a non-transitory computing device-accessible storage medium 230 (also known as a non-transitory computing device-readable storage medium, a non-transitory computing device-readable medium, or a non-transitory computer-readable medium) on which is stored one or more sets of instructions (e.g., the Alertness Monitoring Module 300) embodying any one or more of the methodologies or functions described herein. The one or more sets of instructions may also reside, completely or at least partially, within the main memory 204 and/or within the processing device 202 during execution thereof by the Alertness Monitoring Server 120—the main memory 204 and the processing device 202 also constituting computing device-accessible storage media. The one or more sets of instructions may further be transmitted or received over a network 115 via a network interface device 208.

While the computing device-accessible storage medium 230 is shown in an exemplary embodiment to be a single medium, the term "computing device-accessible storage medium" should be understood to include a single medium or multiple media (e.g., a centralized or distributed database, and/or associated caches and servers) that store the one or more sets of instructions. The term "computing device-accessible storage medium" should also be understood to include any medium that is capable of storing, encoding, or carrying a set of instructions for execution by the computing device and that causes the computing device to include any one or more of the methodologies of the present invention. The term "computing device-accessible storage medium" should accordingly be understood to include, but not be limited to, solid-state memories, optical and magnetic media, etc.

Exemplary System Platform

As noted above, a system, according to various embodiments, is adapted to monitor the alertness of a wearer of a wearable device. Various aspects of the system's functionality may be executed by certain system modules, including the Alertness Monitoring Module 300. The Alertness Monitoring Module 300 is discussed in greater detail below.

Alertness Monitoring Module

Figure 3:
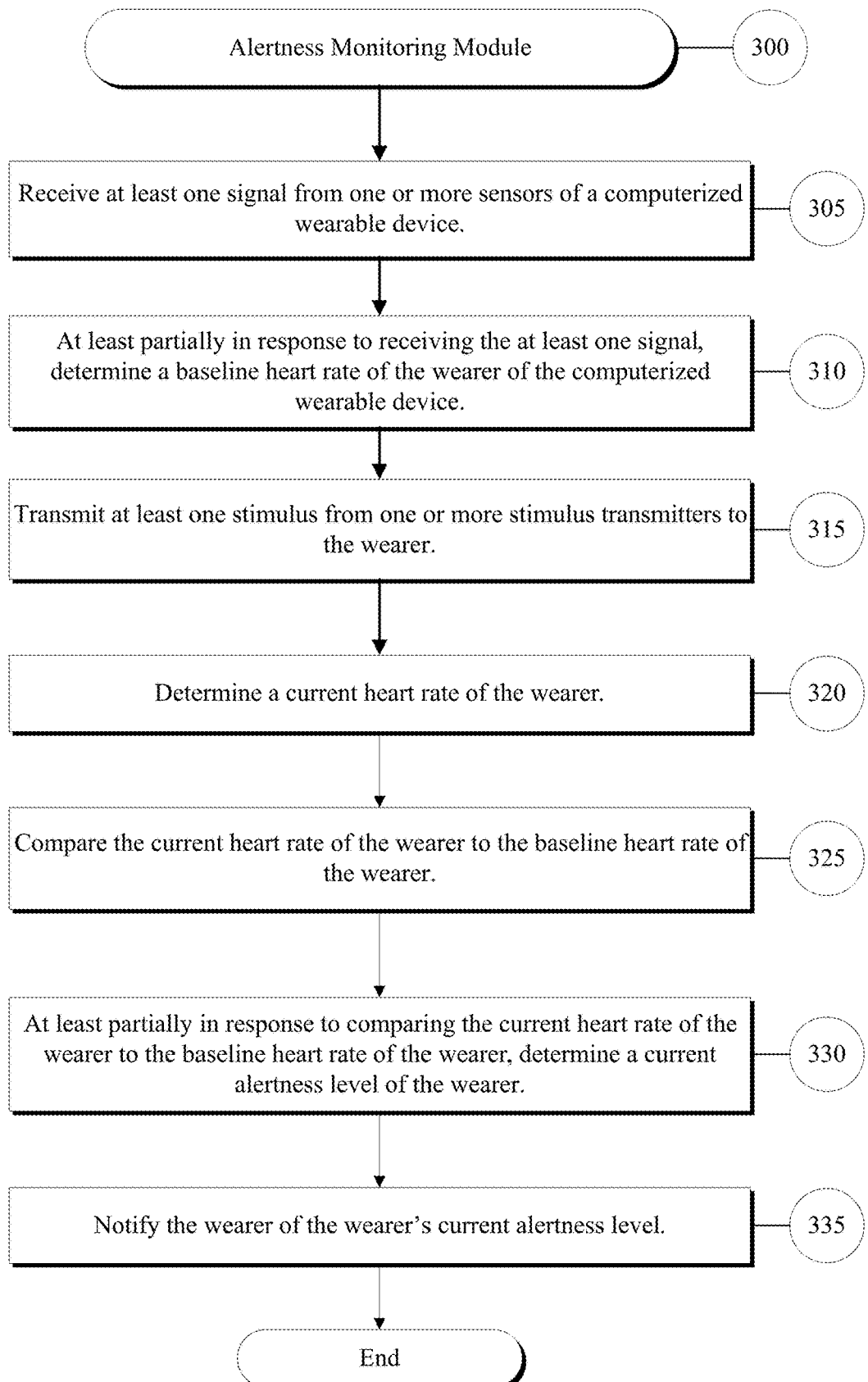
FIG. 3 depicts a flowchart that generally illustrates various steps executed by a Alertness Monitoring Module according to a particular embodiment.

FIG. 3 is a flow chart of operations performed by an exemplary Alertness Monitoring Module 300, which may, for example, run on the Alertness Monitoring Server 120, or any suitable computing device (such as the One or More Health Monitoring Devices 156 or other suitable mobile computing device). In particular embodiments, the Alertness Monitoring Module 300 may determine a wearer's normal alertness and current alertness to determine whether the wearer's current alertness deviates from the wearer's normal alertness.

The system begins, in various embodiments, at Step 305 by receiving at least one signal from one or more sensors of a computerized wearable device. In various embodiments, the one or more sensors are coupled to a computing device that is associated with (e.g., embedded within, attached to) the computerized wearable device or other health monitoring device. In particular embodiments, the computerized wearable device or other health monitoring device comprises at least one processor, computer memory, suitable wireless communications components (e.g., a Bluetooth chip), and a power supply for powering the health monitoring device and/or the various sensors. In various embodiments, the one or more sensors may be adapted to detect one or more characteristics of a wearer of the computerized wearable device, wherein the one or more characteristics of the wearer are associated with the wearer's alertness. In various embodiments, the sensors coupled to the computerized wearable device or other health monitoring device may include, for example, one or more of the following: a heart rate monitor, an electrocardiogram (EKG), a gyroscope, a geomagnetic sensor, a pedometer, a thermometer, a front-facing camera, an eye-facing camera, a microphone, an accelerometer, a magnetometer, a blood pressure sensor, a pulse oximeter, a skin conductance response sensor, a near-field communication sensor, an infrared LED/photodiode sensor combination, a magnetometer, an electrooculography sensor, or any other suitable sensor. In particular embodiments, the sensors coupled to the computerized wearable device comprise one or more of a heart rate monitor, a pulse oximeter, gyroscope, a forward facing camera, and an eye-facing camera.

Figure 4:
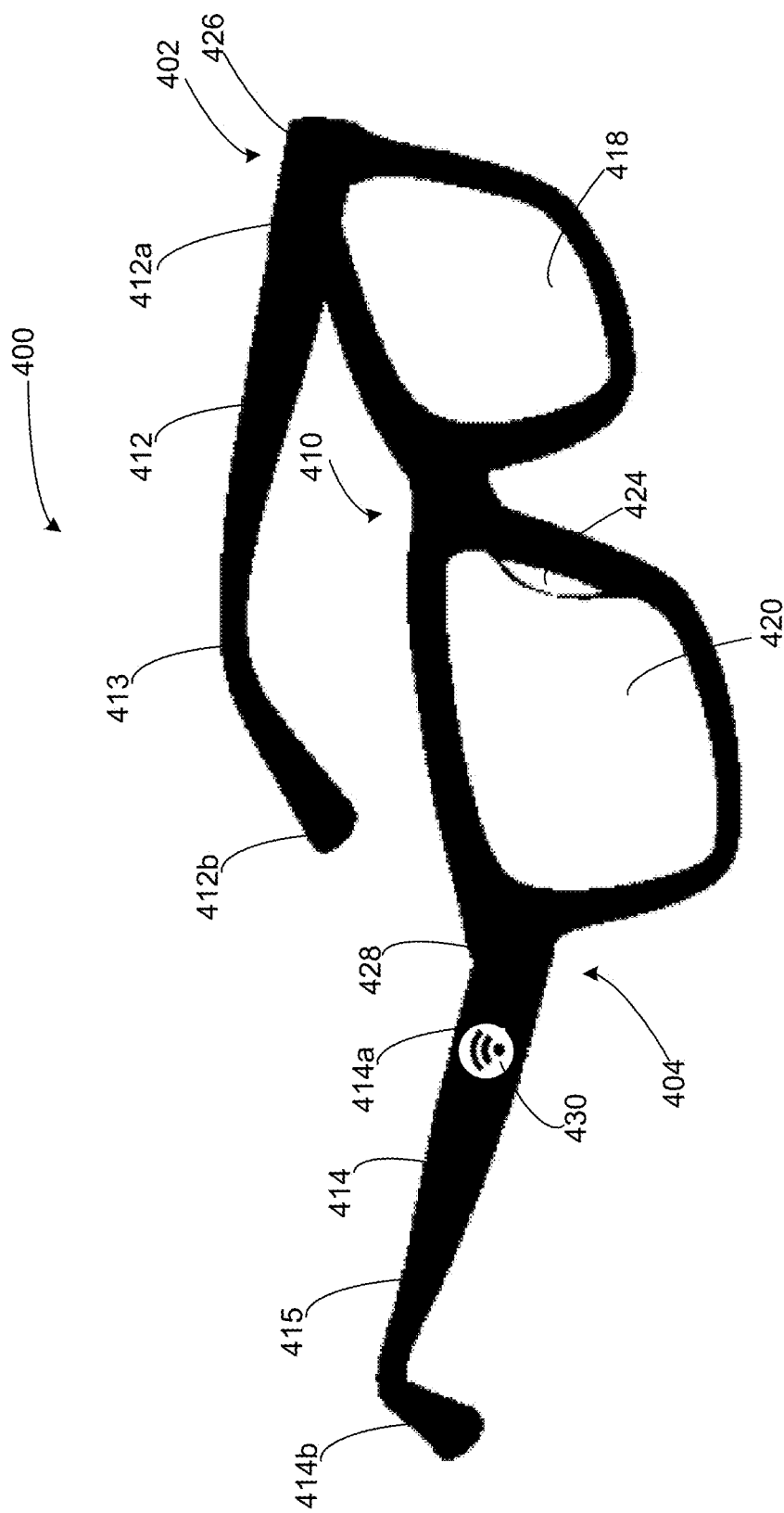
FIG. 4 is an exemplary wearable health monitoring device of FIG. 1.

Referring to FIG. 4, an exemplarily embodiment of a computerized wearable device in the form of eyewear, according to particular embodiments, illustrates that the one or more sensors may be physically coupled to eyewear 400 in any suitable way. For example, in various embodiments, the one or more sensors may be embedded into the eyewear 400. In some embodiments, the one or more sensors may be positioned along the frame 410 of the eyewear 400. In other embodiments, the one or more sensors may be positioned along the temples 412, 414 of the eyewear 400. In still other embodiments, the one or more sensors may be coupled to one or more of the lenses 418, 420 of the eyewear 400. As noted above, the one or more sensors may be coupled to a Bluetooth device that is configured to transmit the one or more signals to a handheld wireless device, and the step of receiving one or more signals from the one or more sensors (discussed below with reference to Step 320) further comprises receiving the one or more signals from the wireless handheld device (e.g., via the Internet, Wi-Fi, a cellular network, etc.). In particular embodiments, one or more of the one or more sensors may be detachable from the eyewear 400. For instance, if a wearer does not need a temperature sensor or other particular sensor, the sensor may be removed from the eyewear. In other embodiments, the one or more sensors may be detached from the eyewear to attach to other portions of the wearer's body. For example, in determining the level of alertness of the wearer, the gyroscope, accelerometer, or other suitable device may be attached to the wearer's back or shoulders and may be adapted to transmit data to the eyewear. The structure of the eyewear will be discussed further below.

Returning to FIG. 3, in particular embodiments, the at least one signal from the one or more sensors may include one or more signals that may be used to derive: (1) the wearer's heart rate; (2) the wearer's heart rhythm; (3) a distance traveled by the wearer; (4) the wearer's body temperature; (5) one or more images associated with the wearer or the wearer's environment; (6) one or more sounds associated with the wearer's body or the wearer's environment; (7) a speed traveled by the wearer; (8) the wearer's blood pressure; (9) the wearer's oxygen saturation level; (10) the wearer's brainwave activity; (11) the wearer's pupil size; (12) the wearer's perspiration level; (13) the wearer's respiratory rate; (14) the number and/or cadence of steps taken by the wearer; (15) the movement of one or more of the wearer's facial muscles; (16) one or more biochemical changes within the wearer's body (e.g., changes in hormone levels, releases of neurotransmitters); (17) changes in the one or more characteristics of the wearer's skin (e.g., skin paleness or clamminess); (18) one or more postures associated with the wearer; and/or (19) measuring the corneo-retinal standing potential that exists between the front and the back of the human eye, (20) any other suitable attribute of the wearer or the wearer's environment. For instance, the system may receive a signal from an eye-facing camera associated with the eyewear that the wearer is looking down at the same time that the system receives a signal from the front-facing camera that there is a road in front of the wearer.

In particular embodiments, the system may receive one or more of the above-referenced signals substantially automatically. In various embodiments, the system may receive one or more of the signals on a substantially periodic basis (e.g., by the second, by the minute, hourly, daily, etc.). For example, the system may receive one or more signals every thirty seconds throughout the day. In other embodiments, the system may receive one or more signals at least partially in response to receiving an indication from the wearer that the system should receive a signal. For instance, the wearer may speak a voice command to the wearable device requesting that the device receive a signal from the gyroscope to get the wearer's orientation. In various embodiments, the system may receive an indication from the wearer of when to have the system receive the signal. For example, the system may receive an indication from the wearer to have the system receive a signal from the gyroscope at 8:00 a.m. and at 2:00 p.m. on a particular day. In particular embodiments, the system may receive a request from the wearer to have a particular signal received from a particular sensor at the same time that the system receives a second particular signal from a second particular sensor. For example, when the system receives a signal that indicates that the wearer's pupil size has changed, the system may, at least partially in response to receiving the changed pupil size signal, also obtain an orientation of the wearer from the gyroscope associated with the eyewear.

In various embodiments, the system may receive one or more signals at least partially in response to receiving an indication from a third party that the system should receive a signal. For instance, the third party may remotely request that the wearable device receive a signal from the heart rate monitor. In some embodiments, the system may receive an indication from the third party of when to have the system receive the signal. For example, the system may receive an indication from the third party (e.g., the wearer's supervisor) to have the system receive a signal from the heart rate monitor every 15 minutes. In particular embodiments, the system may receive a request from the third party to have a particular signal received from a particular sensor at the same time that the system receives a second particular signal from a second particular sensor. For example, when the system receives a signal that indicates that the wearer's heart rate has increased, the system may, at least partially in response to receiving the increased heart rate signal, also obtain an image from the eye-facing camera associated with the eyewear, which may be analyzed by the system to determine why the wearer's heart rate increased.

In some embodiments, the system receives a signal of an image captured by the eyewear. In various embodiments, the system receives a plurality of images captured by the eyewear. In particular embodiments, the system receives the image from the front-facing camera. In some embodiments, the system receives the image substantially automatically from the front-facing camera. In other embodiments, the system may receive the image in response to receiving an indication from the wearer to capture the image. For example, the system may receive a voice command from the wearer to capture the image. In various embodiments, the system may store the captured image in local or remote memory. In some embodiments, the image captured by the eyewear may be a video.

In various embodiments, the system may receive only one signal from a single sensor associated with the eyewear. In other embodiments, the system may receive a signal from a plurality of the sensors associated with the eyewear. In yet other embodiments, the system may receive multiple signals from one or more of the sensors. In various embodiments, the system may be configured to receive a first signal from a first sensor at the same time that it receives a second signal from a second sensor. For example, the system may be configured to receive an image signal from an eye-facing camera associated with the eyewear at the same time that the system receives an orientation signal from the gyroscope associated with the eyewear. As a further example, the system may be configured to simultaneously receive a signal from both an eye-facing camera and a heart rate monitor associated with the eyewear.

At least partially in response to receiving the at least one signal, at Step 310, the system determines a baseline heart rate of the wearer of the computerized wearable device. In particular embodiments, the baseline heart rate of the wearer may be indicative of a normal heart rate of the wearer. In particular embodiments, the baseline heart rate may be a normal starting baseline heart rate of the wearer. For instance, the normal starting baseline heart rate of the wearer when the wearer wakes up may be a resting heart rate range from 60 to 100 beats per minute. In other embodiments, the baseline heart rate may be a desired baseline heart rate of the wearer. For instance, the baseline heart rate may be received from medical guidelines based on a desired baseline heart rate for a wearer of the same sex, height, weight, age, etc. In still other embodiments, the baseline heart rate may be a baseline level of an average person (e.g., not a baseline level based on measurements from the wearer).

In various embodiments, the system may determine the baseline heart rate from a single heart rate monitor. The system may, in some embodiments, determine the baseline heart rate multiple times (e.g., measure the baseline heart rate from the heart rate monitor three times) to create an average baseline heart rate. In various embodiments, the system may be configured to determine the baseline heart rate from the heart rate monitor at the same time that it determines one or more physiological baseline levels from a second sensor. For example, the system may be configured to receive a baseline heart rate at the same time that it receives a position measurement from the accelerometer. In addition, the system may also receive an oxygen saturation level from a pulse oximeter sensor to determine the wearer's blood oxygen level, which may be used in supplementing alertness measurements, balance measurements, and position measurements.

In various embodiments, the system may determine the baseline heart rate substantially automatically after the sensor generates the data. In particular embodiments, the system may determine the baseline heart rate only once to create a static baseline. In some embodiments, the system may determine the baseline heart rate periodically (e.g., by the second, by the minute, hourly, daily, etc.) to create a dynamic baseline. For example, the system may determine the wearer's heart rate every thirty seconds throughout the day to create a dynamic baseline for the wearer's heart rate. In other embodiments, the system may determine the baseline heart rate after receiving an indication from the wearer and/or a third party that the system should determine the one or more baseline levels.

In particular embodiments, the system may determine the baseline heart rate during a predefined time period. In various embodiments, the system may determine the baseline heart rate when a sensor detects movement and/or activities of the wearer (e.g., sitting, lying down, standing, driving a vehicle, flying in an airplane, walking, running, lifting, exercising, etc.). For example, the system may determine the baseline heart rate when the sensor detects that the wearer is driving a vehicle as determined by the speed at which the wearer is currently traveling.

In particular embodiments, the system may store the baseline heart rate in associated memory. In various embodiments, the system may store the baseline heart rate substantially automatically after measuring the data. In other embodiments, the system may store the baseline heart rate after receiving manual input from the wearer and/or a third party requesting that the system store the baseline heart rate. In various embodiments, the system may store the baseline heart rate for a specified period of time. For instance, the system may store the baseline heart rate for a day, a month, a year, etc., in the Database 140. In some embodiments, the system may store the baseline heart rate on any suitable server or other device. In various embodiments, the system may store the baseline heart rate on the Alertness Monitoring Server 120. In particular embodiments, the system may store the baseline heart rate in an account associated with the wearer. In various embodiments, the system may store the baseline heart rate with a timestamp of when the one or more baseline levels were received.

Continuing at Step 315, the system transmits at least one stimulus from one or more stimulus transmitters to the wearer. In various embodiments, the at least one stimulus from the one or more stimulus transmitters may include: (1) a vibration; (2) a change in temperature; (3) a smell; (4) a light; (5) a sound; (6) a shock, (7) or any other suitable stimulus that causes a reaction in the wearer. In particular embodiments, the at least one stimulus is intended to produce a reaction in the wearer (e.g., physical reaction, emotional reaction, neurological reaction, etc.). For example, a particular stimulus may produce an emotional reaction in the wearer causing the wearer to become excited. In some embodiments, the one or more stimulus transmitters may be any suitable transmitter such as: (1) a vibration transmitter; (2) a temperature changing transmitter; (3) a smell transmitter; (4) a light transmitter; (5) a sound transmitter; and (6) a shock transmitter.

In particular embodiments, the one or more stimulus transmitters may be operatively coupled to a vehicle that the wearer drives and/or machinery that the wearer operates. For example, the one or more stimulus transmitters may be configured to generate one or more stimuli from one or more of the following vehicle systems: (1) in-cabin climate control; (2) audio system; (3) engine; (4) in-cabin lighting elements; and (5) brakes. By being operatively coupled to the one or more vehicle systems, the one or more transmitters may be configured to generate one or more stimuli such as: (1) turning up or down the volume on the vehicle's audio system; (2) disabling the driving functionality of the vehicle; (3) turning up or down the temperature on the vehicle's in-cabin climate control; (4) turning on or off the lights in the vehicle's cabin; (5) applying the brakes on the vehicle, (6) etc.

In particular embodiments, the one or more stimulus transmitters may be configured to transmit the at least one stimuli from one or more remote computing devices associated with the wearer and/or a third party. For example, the one or more stimulus transmitters may transmit the at least one stimuli from the wearer's cellphone by causing the cellphone to ring, vibrate, create a flashing light, and/or any other suitable alert. In various embodiments, the system is configured to transmit the one or more stimuli wirelessly (e.g., via a cellular network, Bluetooth, WI-FI, etc.).

At Step 320, the system determines a current heart rate of the wearer. In particular embodiments, the system determines the current heart rate of the wearer at least partially in response to the system transmitting at least one stimulus from the one or more stimulus transmitters to the wearer. In some embodiments, the system determines the current heart rate of the wearer prior to the system transmitting at least one stimulus from the one or more stimulus transmitters to the wearer. In some of these embodiments, the system may also determine the current heart rate of the wearer after the system transmits the at least one stimulus to the wearer. In particular embodiments, the system may determine the current heart rate of the wearer after detecting a change in the wearer's current heart rate. In particular embodiments, the system may determine the current heart rate after receiving an indication from the wearer and/or a third party that the system should determine the current heart rate.

In various embodiments, the system may determine the current heart rate after a predefined time period. In some embodiments, the system may determine the current heart rate when a sensor detects movement and/or activities of the wearer (e.g., sitting, lying down, standing, driving a vehicle, flying in an airplane, walking, running, lifting, exercising, etc.). For example, the system may determine the current heart rate when the sensor detects that the wearer is driving a vehicle as determined by the speed at which the wearer is currently traveling.

The system may, in some embodiments, determine the current heart rate multiple times (e.g., measure the current heart rate from the heart rate monitor three times) to create an average current heart rate. In various embodiments, in addition to determining the current heart rate of the wearer, the system may determine other current physiological attributes of the wearer (e.g., pupil size, oxygen level, blood sugar level, the wearer's gaze and/or changes thereto, perspiration level, respiratory rate, brain wave activity, blink rate, free of physical injuries, injured, asleep, awake, conscious, unconscious, alive, deceased, stable, good, fair, serious, critical, distressed, etc.). In some embodiments, the system may be configured to determine the current heart rate from the heart rate monitor at the same time that it determines one or more current physiological levels from a second sensor. For example, the system may be configured to receive a current heart rate at the same time that it receives a head position measurement from the gyroscope.

In particular embodiments, the system may determine the current heart rate to be an elevated heart rate. In various embodiments, the system may determine the current heart rate to be a normal heart rate. In particular embodiments, the system may determine the current heart rate to be a first particular heart rate for a first period of time and a second particular heart rate for a second period of time.

The system, at Step 325, compares the current heart rate of the wearer to the baseline heart rate of the wearer. In various embodiments, the system compares the wearer's current heart rate to the wearer's baseline heart rate substantially automatically after the system determines the current heart rate of the wearer. In some embodiments, the system may compare the wearer's current heart rate to the wearer's baseline heart rate periodically (e.g., by the second, by the minute, hourly, daily, weekly, monthly, etc.). For example, the system may compare the wearer's current heart rate to the wearer's baseline heart rate every thirty minutes throughout the day. In other embodiments, the system may compare the wearer's current heart rate to the wearer's baseline heart rate after receiving an indication from the wearer or a third party that the system should compare the wearer's current heart rate to the wearer's baseline heart rate. In various embodiments, the system may receive an indication from the wearer and/or a third party of when to have the system compare the wearer's current heart rate to the wearer's baseline heart rate. For example, the system may receive an indication from the wearer to have the system compare the wearer's current heart rate to the baseline heart rate of the wearer at 6:00 a.m. and at 2:30 p.m. on a particular day.

In various embodiments, the system may compare the wearer's current heart rate to the wearer's baseline heart rate to determine if the wearer's current heart rate deviates from the wearer's baseline heart rate. In particular embodiments, the wearer's current heart rate may not deviate from the wearer's baseline heart rate. In some embodiments, the wearer's current heart rate may deviate from the wearer's baseline heart rate. In particular embodiments, the system may detect one or more deviations from the wearer's baseline heart rate. In various embodiments, the system may determine the wearer's current heart rate deviates from the wearer's baseline heart rate based on a predetermined percentage. For instance, the system may determine a wearer's current heart rate deviates from the wearer's baseline heart rate if the wearer's current heart rate is 10% faster than the wearer's baseline heart rate. In particular embodiments, the system may store the comparisons in an account associated with the wearer. In some embodiments, the comparisons may be accessible by the wearer and/or a third party. For instance, the comparisons may be diagramed in a chart that is accessible from the wearable device or from a computing device by the wearer's employer.

At least partially in response to comparing the current heart rate of the wearer to the baseline heart rate of the wearer, at Step 330, the system determines a current alertness level of the wearer. In particular embodiments, the system may determine the current alertness level of the wearer by calculating an amount of time it takes the current heart rate of the wearer to return from an elevated heart rate that results from the one or more stimuli to about the baseline heart rate of the wearer. In some embodiments, the system may set a predetermined amount of time that it takes the current heart rate of the wearer to return from an elevated heart rate to about the baseline heart rate of the wearer as a normal amount of time. In particular embodiments, the system may set a range of time as a normal amount of time for the wearer's heart rate to return from the elevated heart rate to the baseline heart rate. For example, the predetermined amount of time may be a range between 60 seconds and 300 seconds. In various embodiments, the system may determine whether the amount of time it takes the current heart rate of the wearer to return from the elevated heart rate that results from the one or more stimuli to the baseline heart rate of the wearer is above a particular heart rate threshold value. In particular embodiments, the system may determine the current alertness level of the wearer to be a particular alertness level for a particular period of time. For example, the system may determine that the wearer has been awake for over 15 hours.

In some embodiments, the system may determine the wearer's level of alertness based on the amount of time that it takes for the wearer's current heart rate to return to a particular deviation from the wearer's baseline heart rate. For example, the wearer's alertness level may be determined based on the amount of time it takes the wearer's current heart rate to fall to within a 5% range about the wearer's baseline heart rate. In particular, if the wearer's baseline heart rate is 75 beats per minute and the current hear rate is 120 beats per minute, then the system may determine the amount of time it takes for the current heart rate to get to within 5% of the baseline heartrate (e.g., 79 beats per minute.

In various embodiments, the system may determine the current alertness of the wearer based on the one or more physical attributes of the wearer (e.g., pupil size, heart rate, perspiration level, respiratory rate, brain wave activity, free of physical injuries, injured, asleep, awake, conscious, unconscious, alive, deceased, stable, good, fair, serious, critical, distressed, etc.).

In particular embodiments, the system may store the current alertness of the wearer in an account associated with the wearer. In some embodiments, the current alertness of the wearer may be accessible by the wearer and/or a third party. For instance, the current alertness of the wearer may be diagramed in a chart that is accessible from the wearable device or from a computing device by the wearer's supervisor. In various embodiments, the system may store the current alertness of the wearer in the Database 140.

At Step 335, the system notifies the wearer of the wearer's current alertness level. In various embodiments, the system may notify a third party of the wearer's current alertness level. In particular embodiments, the system may notify the wearer and/or a third party when the wearer's current alertness deviates from the wearer's baseline alertness. In some embodiments, in addition to notifying the wearer, the system may update the wearer's account to note that a notification was sent. In particular embodiments, the system may notify the wearer of the deviation from the baseline alertness by displaying an image on the lens of the eyewear. In other embodiments, the system notifies the wearer of the deviation from the baseline alertness by communicating through a speaker to the wearer. In various embodiments, the system may notify the wearer of the deviation from the baseline alertness by sending an electric shock to the wearer. In particular embodiments, the system may notify the wearer by generating an alert from one or more of the following vehicle systems: (1) in-cabin climate control; (2) audio system; (3) engine; (4) in-cabin lighting elements; and (5) brakes. By being operatively coupled to the one or more vehicle systems, the system may be configured to generate one or more alerts such as: (1) turning up or down the volume on the vehicle's audio system; (2) disabling the driving functionality of the vehicle; (3) turning up or down the temperature on the vehicle's in-cabin climate control; (4) turning on or off the lights in the vehicle's cabin; (5) applying the brakes on the vehicle, (6) etc.

In some embodiments, the system notifies the wearer and/or the third party of the deviation from the baseline alertness by sending a notification to the wearer's and/or the third party's mobile device. In particular embodiments, the system notifies the wearer and/or the third party of the deviation from the baseline alertness by email and/or text message. In other embodiments, the system may notify the wearer and/or the third party of a single deviation from the normal alertness substantially immediately after the system detects the deviation between the wearer's current alertness as compared to the wearer's normal alertness.

In various embodiments, the system may notify the wearer and/or the third party of the deviation from the normal alertness after a particular event. For example, the system may notify a third party of the wearer's current alertness if the system determines that the wearer's vehicle has swerved. In some embodiments, the system may notify the wearer and/or the third party of the deviation from the normal alertness after a particular period of time. For instance, the system may notify the wearer of the deviation from the wearer's normal alertness to a current alertness of drowsy after one minute of detecting the wearer being drowsy. In particular embodiments, at least partially in response to determining that the amount of time it takes the current heart rate of the wearer to return from an elevated heart rate that results from the one or more stimuli to about the baseline heart rate of the wearer is above a particular heart rate threshold value, the system may generate an alert that the wearer is tired.

In various embodiments, at least partially in response to determining that the wearer has experienced an impact, the system may notify one of the wearer or a third party that the wearer has experienced an impact. For example, if the wearer becomes drowsy and experiences an impact due to the vehicle's airbag deploying caused by the vehicle being involved in an accident, the system may notify the wearer's supervisor that the wearer has experienced an impact.

In various embodiments, in addition to notifying the wearer of the deviation from the normal alertness, the system may also provide suggestions to the wearer on how to change the wearer's current alertness to make it conform to the wearer's normal alertness. For instance, where the wearer's normal alertness while driving is alert and attentive and the wearer's current alertness while driving is drowsy, the system may suggest for the wearer to pull the vehicle over and rest. In some embodiments, the system may also provide suggestions to the wearer on the cause of the wearer's current alertness level. For example, where the wearer's normal alertness is alert and the wearer's current alertness is drowsy, the system may provide a suggestion to the wearer that the cause of the wearer's current alertness may be fatigue or a more serious medical issue such as depression based on the wearer's frequency of being drowsy. In addition to using the wearer's heartbeat to determine the wearer's level of alertness, the system may use information about one or more of the wearer's pulse oximeter lever, blood pressure level, pupil response, etc. to determine the cause of the wearer's alertness level.

In various embodiments, the system, when executing the Alertness Monitoring Module 300, may omit particular steps, perform particular steps in an order other than the order presented above, or perform additional steps not discussed directly above.

Structure of the Eyewear

Referring again to FIG. 4, eyewear 400, according to various embodiments, includes: (1) the eyewear frame 410; (2) the first temple 412; and (3) the second temple 414. These various components are discussed in more detail below.

Eyewear Frame

Referring still to FIG. 4, eyewear 400, in various embodiments, includes any suitable eyewear frame 410 configured to support one or more lenses 418, 420. In the embodiment shown in this figure, the eyewear frame 410 has a first end 402 and a second end 404. The eyewear frame 410 may be made of any suitable material such as metal, ceramic, polymers or any combination thereof. In particular embodiments, the eyewear frame 410 is configured to support the first and second lenses 418, 420 about the full perimeter of the lenses. In other embodiments, the eyewear frame 410 may be configured to support the first and second lenses 418, 420 about only a portion of each respective lens. In various embodiments, the eyewear frame 410 is configured to support a number of lenses other than two lenses (e.g., a single lens, a plurality of lenses, etc.). In particular embodiments, the lenses 418, 420 may include prescription lenses, sunglass lenses, or any other suitable type of lens (e.g., reading lenses, non-prescription lenses), which may be formed from glass or polymers.

The eyewear frame 410 includes a first (not shown in figure) and second nose pad 424, which may be configured to maintain the eyewear 400 adjacent the front of a wearer's face such that the lenses 418, 420 are positioned substantially in front of the wearer's eyes while the wearer is wearing the eyewear 400. In particular embodiments, the nose pads may comprise a material that is configured to be comfortable when worn by the wearer (e.g., rubber, polymer, etc.). In other embodiments, the nose pads may include any other suitable material (e.g., plastic, metal, etc.). In still other embodiments, the nose pads may be integrally formed with the frame 410 and made from the same material as the frame.

The eyewear frame 410 includes a first and a second hinge 426, 428, that attach the first and second temples 412, 414 to the frame first and second ends 402, 404, respectively. In various embodiments, the hinges may be formed by any suitable connection (e.g., tongue and groove, ball and socket, spring hinge, etc.). In particular embodiments, the first hinge 426 may be welded to, or integrally formed with, the frame 410 and the first temple 412 and the second hinge 428 may be welded to, or integrally formed with, the frame 410 and the second temple 414.

First and Second Temples

As shown in FIG. 4, the first temple 412, according to various embodiments, is rotatably connected to the frame 410 at a right angle to extend the first temple 412 substantially perpendicular, substantially parallel, or anywhere in between the right angle to the frame 410. The first temple 412 has a first and second end 412a, 412b. Proximate the first temple second end 412b, the first temple 412 includes an earpiece 413 configured to be supported by a wearer's ear. Similarly, the second temple 414, according to various embodiments, is rotatably connected to the frame 410 at a right angle to extend the second temple 414 substantially perpendicular, substantially parallel, or anywhere in between the right angle to the frame 410. The second temple 414 has a first and second end 414a, 414b. Proximate the second temple second end 414b, the second temple 414 includes an earpiece 415 configured to be supported by a wearer's ear.

Sensors

In various embodiments, the second temple 414 has one or more sensors 430 connected to the second temple 414. As discussed above, in various embodiments, the one or more sensors 430 may be coupled to the frame 410, the first and second temples 412, 414, the first and second lenses 418, 410, or any other portion (e.g., the nose pads, etc.) of the eyewear 400 in any suitable way. For instance, the one or more sensors 430 may be embedded into the eyewear 400, coupled to the eyewear 400, and/or operatively coupled to the eyewear 400. In various embodiments, the one or more sensors 430 may be formed at any point along the eyewear 400. For instance, a fingerprint reader may be disposed adjacent the first temple of the eyewear 400. In various embodiments, the one or more sensors 430 may be formed in any shape. In addition, the one or more sensors 430 may be formed on the inner (back) surface of the frame 410, the first and second temples 412, 414, the first and second lenses 418, 410, or any other portion of the eyewear 400. In other embodiments, the one or more sensors 430 may be formed on the outer (front) surface of the frame 410, the first and second temples 412, 414, the first and second lenses 418, 410, or any other portion of the eyewear 400.

In various embodiments, the one or more sensors 430 that are coupled to the eyewear (or other wearable device) are adapted to detect one or more characteristics of the eyewear or a wearer of the eyewear, wherein the one or more characteristics of the eyewear or the wearer are associated with the wearer's physiology. In various embodiments, the one or more sensors coupled to the eyewear or other wearable device may include, for example, one or more of the following: a near-field communication sensor, a Bluetooth chip, a GPS unit, an RFID tag (passive or active), a fingerprint reader, an iris reader, a retinal scanner, a voice recognition sensor, a heart rate monitor, an electrocardiogram (EKG), an electroencephalogram (EEG), a pedometer, a thermometer, a front-facing camera, an eye-facing camera, a microphone, an accelerometer, a magnetometer, a blood pressure sensor, a pulse oximeter, a skin conductance response sensor, any suitable biometric reader, an infrared LED sensor, a photodiode sensor, a magnetometer, or any other suitable sensor. In some embodiments, the one or more sensors may include a unique shape, a unique code, or a unique design physically inscribed into the eyewear that may be readable by an individual or a remote computing device.

In various embodiments, the one or more sensors are coupled to a computing device that is associated with (e.g., embedded within, attached to) the eyewear or other wearable device. In particular embodiments, the eyewear or other wearable device comprises at least one processor, computer memory, suitable wireless communications components (e.g., a Bluetooth chip) and a power supply for powering the wearable device and/or the various sensors.

As noted above, the one or more sensors may be coupled to a Bluetooth device that is configured to transmit the one or more signals to a handheld wireless device, and the step of using the eyewear to measure the baseline heart rate from the one or more sensors (discussed above in reference to Step 310) further comprises receiving the one or more signals from the wireless handheld device (e.g., via the Internet). In particular embodiments, one or more of the sensors may be detachable from the eyewear. For instance, if a wearer does not need a temperature sensor or other particular sensor, the sensor may be removed from the eyewear.

Exemplary User Experience

Monitor Driver Alertness

In a particular example of a wearer using the Alertness Monitoring Module 300 to determine their alertness, the wearer may put on the wearable device (e.g., computerized eyewear) as the wearer enters a vehicle to begin driving. During this time, the system tracks the alertness of the wearer using the system's heart rate sensor, orientation sensor(s), brainwave activity sensor, blink rate sensor, oxygen sensor, infrared LED, photodiode sensor, EOG sensor, front-facing camera, and/or eye-facing camera. The wearer may begin by having the system take a baseline measurement of the wearer's heart rate while the wearer is looking straight ahead out of the windshield of the vehicle. The wearer's baseline heart rate may be determined to be in the normal range for an individual with a similar height, weight, sex, age, etc. The system then tracks the heart rate of the wearer to determine any changes in the wearer's heart rate. If the wearer's heart rate remains relatively unchanged for a predetermined period of time, the system may stimulate the wearer's heart rate by producing a vibration from the wearer's cellphone. If the wearer's heart rate remains above a predetermined heart rate threshold for longer than a predetermined period of time, the system may determine that the wearer is drowsy or that the wearer's level of alertness is impaired from an expected level of alertness. The system may alert the wearer that the wearer is drowsy by decreasing the temperature in the vehicle driven by the wearer. This may cause the wearer to again become alert. If the wearer does not become appropriately alert, the system may generate an alert to a computing device associated with a third party, such as a supervisor for the wearer. In another example, the wearer's blink rate and/or blink frequency may increase or decrease based on the wearer's alertness level. For instance, where the wearer has become tired, the wearer's frequency of blinks may decrease as the wearer's eyes remain closed for longer periods of time or remains open and fixated as the wearer's level of alertness is diminished. The system may then determine that the wearer's current alertness deviates from the wearer's normal alertness. In response to determining a particular deviation from the wearer's normal alertness level (e.g., as determined by changes in the wearer's blink rate), the system may emit a sound, or other alert, to notify the wearer (or other individual) that the wearer's alertness level is too low to be driving.

CONCLUSION

Many modifications and other embodiments of the invention will come to mind to one skilled in the art to which this invention pertains, having the benefit of the teaching presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. A computerized eyewear comprising:
   a. at least one processor;
   b. one or more sensors operatively coupled to the at least one processor, the one or more sensors selected from the group consisting of:
      i. a heart rate monitor,
      ii. a pulse oximeter,
      iii. a gyroscope
      iv. a forward facing camera, and
      v. an eye-facing camera;
   c. a power source operatively coupled to the at least one processor; and
   d. a communication device operatively coupled to the at least one processor;
   wherein the computerized eyewear is operatively coupled to a vehicle that a wearer is driving and is configured to:
      i. receive at least one signal from the one or more sensors on the computerized wearable device;
      ii. at least partially in response to receiving the at least one signal, determine a current alertness of the wearer of the computerized eyewear;
      iii. at least partially in response to determining the current alertness of the wearer, compare the current alertness of the wearer to a normal alertness of the wearer; and iv. notify the wearer when the current alertness of the wearer deviates from the normal alertness of the wearer by generating an alert selected from the group consisting of:
1. turning up the volume on the vehicle's audio system;
2. disabling driving functionality of the vehicle; and
3. decreasing the temperature on the vehicle's in-cabin climate control.

2. The computerized eyewear of claim 1, wherein
a. the one or more sensors comprises a heart rate monitor; and
b. the computerized eyewear is further configured to:
i. receive a signal from the heart rate monitor;
ii. determine a current heart rate of the wearer at least partially based on the received signal from the heart rate monitor; and
iii. compare the current heart rate of the wearer to a baseline heart rate of the wearer.

3. The computerized eyewear of claim 1, wherein
a. the one or more sensors comprises a gyroscope; and
b. the computerized eyewear is further configured to:
i. receive one or more signals from the gyroscope;
ii. determine a current pitch, roll, and yaw of the wearer's head at least partially based on the received one or more signals from the gyroscope; and
iii. compare the current pitch, roll, and/or yaw of the wearer's head to a baseline pitch, roll, and/or yaw of the wearer's head.

4. The computerized eyewear of claim 3, wherein the computerized eyewear if further configured to notify the wearer when the current pitch, roll, and/or yaw deviates from the baseline pitch, roll, and yaw by a predetermined amount.

5. The computerized eyewear of claim 1, wherein
a. the one or more sensors further comprises a blink rate sensor; and
b. the computerized eyewear is further configured to:
i. receive a signal from the blink rate sensor;
ii. determine a current blink rate of the wearer at least partially based on the received signal from the blink rate sensor;
iii. determine whether the current blink rate is below a particular blink rate threshold value; and
iv. at least partially in response to determining that the current blink rate is below the particular blink rate threshold value, generate an alert indicating that the wearer is tired.

6. A computer-implemented method of determining an alertness of a wearer of a computerized wearable device the method comprising:
a. receiving, by a processor, at least one signal from one or more sensors of the computerized wearable device;
b. at least partially in response to receiving the at least one signal, determining, by a processor, a baseline heart rate of the wearer of the computerized wearable device;
c. transmitting, by a processor, at least one stimulus from one or more stimulus transmitters to the wearer;
d. determining, by a processor, a current heart rate of the wearer;
e. comparing, by a processor, the current heart rate of the wearer to the baseline heart rate of the wearer;
f. at least partially in response to comparing the current heart rate of the wearer to the baseline heart rate of the wearer, determining, by a processor, a current alertness level of the wearer by i. calculating, by a processor, an amount of time it takes the current heart rate of the wearer to return from an elevated heart rate that results from the one or more stimuli to about the baseline heart rate of the wearer;
ii. determining, by a processor, whether the amount of time it takes the current heart rate of the wearer to return to about the baseline heart rate is above a particular threshold value; and
iii. at least partially in response to determining that the amount of time it takes the current heart rate to return to about the baseline heart rate is above a particular threshold value, generating, by a processor, an alert that the wearer is tired; and
g. notifying, by a processor, the wearer of the wearer's current alertness level.

7. The computer-implemented method of claim 6, further comprising providing a computer wearable device comprising one or more sensors coupled to the computerized wearable device, the one or more sensors being adapted to detect one or more physiological characteristics of the wearer of the computerized wearable device, wherein
a. the one or more characteristics are associated with the wearer's alertness and one or more stimulus transmitters coupled to the computerized wearable device, the one or more stimulus transmitters being adapted to initiate the transmission of one or more stimuli,
b. the computerized wearable device is eyewear having the one or more sensors, a power source, and a communication device coupled thereto.

8. The computer-implemented method of claim 6, wherein the one or more stimuli are selected from the group consisting of:
a. a shock,
b. a vibration,
c. a sound, and
d. a flashing light.

9. The computer-implemented method of claim 6, wherein generating the alert that the wearer is tired comprises sending a notification to a computing device associated with a third party.

10. The computer-implemented method of claim 6, wherein generating the alert that the wearer is tired comprises sending a notification to a computing device associated with the wearer.

11. The computer-implemented method of claim 6, wherein the computerized wearable device is further operatively coupled to a vehicle that the wearer is driving.

12. The computer-implemented method of claim 11, wherein generating the alert that the wearer is tired comprises turning up the volume on the vehicle's audio system.

13. The computer-implemented method of claim 11, wherein generating the alert that the wearer is tired comprises disabling driving functionality of the vehicle.

14. The computer-implemented method of claim 11, wherein generating the alert that the wearer is tired comprises decreasing the temperature on the vehicle's in-cabin climate control.

15. A computer system for determining the alertness of a wearer of a computerized wearable device, the computer wearable device comprising:
a. one or more sensors coupled to the computerized wearable device, the one or more sensors being adapted to detect one or more physiological characteristics of the wearer of the computerized wearable device, wherein the one or more characteristics are associated with the wearer's alertness; and b. at least one processor operatively coupled to the one or more sensors, wherein the at least one processor is configured for:
  i. receiving at least one signal from the one or more sensors of the computerized wearable device;
  ii. at least partially in response to receiving the at least one signal, measuring one or more baseline heart rates of the wearer of the computerized wearable device that are indicative of a normal heart rate of the wearer;
  iii. receiving at least another signal from the one or more sensors of the computerized wearable device, wherein the at least another signal indicates a current heart rate of the wearer;
  iv. calculating a predetermined heart rate threshold value based on the wearer's baseline heart rate;
  v. determining that the current heart rate of the wearer is above the predetermined heart rate threshold value that corresponds to an excited state of the wearer;
  vi. calculating a length of time that the current heart rate of the wearer remains above the predetermined heart rate threshold value;
  vii. at least partially in response to the length of time that the current heart rate of the wearer stays above the predetermined heart rate threshold value, determining the current alertness level of the wearer; and
  viii. notifying the wearer of the wearer's current alertness level.

16. The computer system of claim 15, wherein the at least one processor is further configured for:
  a. calculating an amount of time it takes the current heart rate of the wearer to return to the normal heart rate of the wearer;
  b. determining whether the amount of time it takes the current heart rate of the wearer to return to the normal heart rate of the wearer is above a particular time threshold value;
  c. at least partially in response to determining that the amount of time it takes the current heart rate of the wearer to return to the normal heart rate of the wearer is above the particular time threshold value, generating an alert indicating that the wearer is tired.

17. The computer system of claim 15, wherein:
a. the computerized wearable device comprises one or more stimulus transmitters coupled to the computerized wearable device, the one or more stimulus transmitters being adapted to transmit one or more stimuli to the wearer of the computerized wearable device; and
b. the at least one processor is further configured for:
  i. determining that the current heart rate of the wearer has been within a predetermined range of the normal heart rate for a predetermined amount of time;
  ii. at least partially in response to determining that the current heart rate of the wearer has been within the predetermined range of the normal heart rate for the predetermined amount of time, transmitting at least one stimulus from the one or more stimulus transmitters;
  iii. calculating a second length of time it takes the current heart rate of the wearer to return to the normal heart rate of the wearer;
  iv. determining whether the second length of time it takes the current heart rate of the wearer to return to the normal heart rate of the wearer is above a particular time threshold value;
  v. at least partially in response to determining that the second length of time it takes the current heart rate of the wearer to return to the normal heart rate of the wearer is above the particular time threshold value, generating an alert indicating that the wearer is tired.

18. The computer system of claim 17, wherein the particular time threshold value comprises a range between 60 seconds and 300 seconds.

* * * * *

UNITED STATES PATENT AND TRADEMARK OFFICE
CERTIFICATE OF CORRECTION

PATENT NO. : 10,617,342 B2
APPLICATION NO. : 15/611574
DATED : April 14, 2020
INVENTOR(S) : Jay William Sales, Richard Chester Klosinski, Jr. and Matthew Allen Workman Page 1 of 1

It is certified that error appears in the above-identified patent and that said Letters Patent is hereby corrected as shown below:

On the Title Page

Column 2, Lines 23-24 In References Cited - Other Publications, on page 5, "Office Action, dated October 4, 2019, from corresponding U.S. Application No. 15/191,196" should read --Office Action, dated October 4, 2019, from corresponding U.S. Application No. 15/791,196--.

Signed and Sealed this
Fourteenth Day of July, 2020

Andrei Iancu
*Director of the United States Patent and Trademark Office*